(12) United States Patent
Marczyk et al.

(10) Patent No.: US 10,278,720 B2
(45) Date of Patent: *May 7, 2019

(54) PEDIATRIC COMBINATION SURGICAL DEVICE

(71) Applicant: Covidien LP, Mansfield, MA (US)

(72) Inventors: Stanislaw Marczyk, Stratford, CT (US); Christopher Switalski, Suffield, CT (US); Russell Pribanic, Roxbury, CT (US)

(73) Assignee: Covidien LP, Mansfield ( * ) Notice: Subject to any disclaimer, the term of this patent is extended or adjusted under 35 U.S.C. 154(b) by 304 days.

This patent is subject to a terminal disclaimer.

(21) Appl. No.: 15/252,366

(22) Filed: Aug. 31, 2016

(65) Prior Publication Data

US 2016/0367277 A1 Dec. 22, 2016

Related U.S. Application Data

(63) Continuation of application No. 14/102,546, filed on Dec. 11, 2013, now Pat. No. 9,439,665.

(Continued)

(51) Int. Cl.
*A61B 17/29* (2006.01)
*A61B 17/295* (2006.01)
(Continued)

(52) U.S. Cl.
CPC ...... *A61B 17/295* (2013.01); *A61B 17/00234* (2013.01); *A61B 17/285* (2013.01);
(Continued)

(58) Field of Classification Search
CPC . A61B 17/00234; A61B 17/285; A61B 17/29; A61B 17/2909; A61B 17/295;
(Continued)

(56) References Cited

U.S. PATENT DOCUMENTS

| 5,133,736 A | 7/1992 | Bales, Jr. et al. |
| 5,214,968 A | 6/1993 | Kenney |

(Continued)

FOREIGN PATENT DOCUMENTS

| CN | 2092023 U | 1/1992 |
| KR | 20040087806 A | 10/2004 |

(Continued)

OTHER PUBLICATIONS

European Search Report dated Mar. 17, 2014 in European Application No. 13 19 8294.

*Primary Examiner* — Michael F Peffley

(57) ABSTRACT

A combination surgical device is provided and includes a dissection blade moveably mounted in a first jaw of the surgical device. The surgical device includes a second jaw movably mounted relative to the first jaw and a handle assembly. The handle assembly includes an advancement mechanism for incrementally advancing the blade out of the first jaw and a lever to open and close the first and second jaws. A lock member is provided to maintain the blade in an extended condition and a release lever is provided to disable the lock member. The surgical device additionally includes a safety or lock out mechanism which prevents the jaws from moving while the blade is in the extended condition.

19 Claims, 28 Drawing Sheets

Related U.S. Application Data

(60) Provisional application No. 61/739,858, filed on Dec. 20, 2012.

(51) Int. Cl.
| | | |
|---|---|---|
| *A61B 17/285* | (2006.01) | |
| *A61B 18/08* | (2006.01) | |
| *A61B 17/00* | (2006.01) | |
| *A61B 17/3211* | (2006.01) | |
| *A61B 17/32* | (2006.01) | |
| *A61B 90/00* | (2016.01) | |
| *A61B 18/14* | (2006.01) | |

(52) U.S. Cl.
CPC ...... *A61B 17/2909* (2013.01); *A61B 17/3211* (2013.01); *A61B 18/085* (2013.01); *A61B 2017/00353* (2013.01); *A61B 2017/00407* (2013.01); *A61B 2017/320044* (2013.01); *A61B 2017/32113* (2013.01); *A61B 2018/1412* (2013.01); *A61B 2090/0811* (2016.02)

(58) Field of Classification Search
CPC .............. A61B 17/3211; A61B 18/085; A61B 2017/00353; A61B 2017/00407; A61B 2017/320044; A61B 2017/32113
See application file for complete search history.

(56) References Cited

U.S. PATENT DOCUMENTS

| | | | |
|---|---|---|---|
| 5,263,967 A | 11/1993 | Lyons, III et al. | |
| 5,312,434 A | 5/1994 | Crainich | |
| 5,330,502 A | 7/1994 | Hassler et al. | |
| 5,331,971 A | 7/1994 | Bales et al. | |
| 5,342,390 A | 8/1994 | Slater et al. | |
| 5,396,900 A | 3/1995 | Slater et al. | |
| 5,439,478 A | 8/1995 | Palmer | |
| 5,478,351 A | 12/1995 | Meade et al. | |
| 5,489,292 A | 2/1996 | Tovey et al. | |
| 5,501,698 A | 3/1996 | Roth et al. | |
| 5,509,922 A | 4/1996 | Aranyi et al. | |
| 5,695,521 A | 12/1997 | Anderhub | |
| 5,707,392 A | 1/1998 | Kortenbach | |
| 5,716,374 A | 2/1998 | Francese et al. | |
| 5,718,714 A | 2/1998 | Livneh | |
| 5,722,421 A | 3/1998 | Francese et al. | |
| 5,782,859 A | 7/1998 | Nicholas et al. | |
| 5,797,958 A | 8/1998 | Yoon | |
| 5,827,323 A | 10/1998 | Klieman et al. | |
| 5,893,874 A | 4/1999 | Bourque et al. | |
| 5,893,875 A | 4/1999 | O'Connor et al. | |
| 5,895,361 A | 4/1999 | Turturro | |
| 5,928,256 A | 7/1999 | Riza | |
| 6,010,523 A | 1/2000 | Sabin et al. | |
| 6,024,741 A | 2/2000 | Williamson, IV et al. | |
| 6,033,404 A * | 3/2000 | Melzer | A61B 18/1482 606/41 |
| 6,315,777 B1 | 11/2001 | Comben | |
| 6,358,268 B1 | 3/2002 | Hunt et al. | |
| 6,440,085 B1 | 8/2002 | Krzyzanowski | |
| 6,582,451 B1 | 6/2003 | Marucci et al. | |
| 6,709,445 B2 | 3/2004 | Boebel et al. | |
| 7,118,587 B2 * | 10/2006 | Dycus | A61B 17/2909 606/205 |
| 7,208,005 B2 | 4/2007 | Frecker et al. | |
| 7,232,440 B2 * | 6/2007 | Dumbauld | A61B 18/1445 606/45 |
| 7,331,978 B2 | 2/2008 | Haluck | |
| 7,341,564 B2 | 3/2008 | Zwiefel et al. | |
| 7,367,976 B2 * | 5/2008 | Lawes | A61B 18/1445 606/41 |
| 7,775,989 B2 | 8/2010 | Nakao | |
| D649,249 S * | 11/2011 | Guerra | D24/146 |
| 8,096,956 B2 | 1/2012 | George et al. | |
| 8,114,122 B2 | 2/2012 | Nau, Jr. | |
| 8,133,254 B2 | 3/2012 | Dumbauld et al. | |
| 8,246,618 B2 | 8/2012 | Bucciaglia et al. | |
| 8,388,647 B2 | 3/2013 | Nau, Jr. et al. | |
| 8,469,992 B2 | 6/2013 | Roy et al. | |
| 8,512,371 B2 | 8/2013 | Kerr et al. | |
| 8,556,929 B2 | 10/2013 | Harper et al. | |
| 8,628,557 B2 | 1/2014 | Collings et al. | |
| 8,632,564 B2 | 1/2014 | Cunningham | |
| 9,439,665 B2 | 9/2016 | Marczyk et al. | |
| 2002/0128675 A1 | 9/2002 | Randall | |
| 2005/0054946 A1 | 3/2005 | Krzyzanowski | |
| 2005/0113827 A1 | 5/2005 | Dumbauld et al. | |
| 2006/0129146 A1 | 6/2006 | Dycus et al. | |
| 2006/0184198 A1 | 8/2006 | Bales et al. | |
| 2006/0259071 A1 | 11/2006 | Nicholas et al. | |
| 2007/0073185 A1 | 3/2007 | Nakao | |
| 2007/0162072 A1 | 7/2007 | Nicholas et al. | |
| 2008/0027468 A1 | 1/2008 | Fenton et al. | |
| 2010/0023050 A1 | 1/2010 | Reinauer et al. | |
| 2011/0034918 A1 | 2/2011 | Reschke | |
| 2012/0296371 A1 | 11/2012 | Kappus et al. | |
| 2012/0316541 A1 | 12/2012 | Young et al. | |
| 2012/0316601 A1 | 12/2012 | Twomey | |
| 2013/0046337 A1 | 2/2013 | Evans et al. | |
| 2013/0085412 A1 | 4/2013 | Timberlake et al. | |
| 2013/0123837 A1 | 5/2013 | Roy et al. | |
| 2013/0238016 A1 | 9/2013 | Garrison | |
| 2013/0296922 A1 | 11/2013 | Allen, IV et al. | |
| 2013/0296923 A1 | 11/2013 | Twomey et al. | |
| 2013/0325057 A1 | 12/2013 | Larson et al. | |
| 2014/0066966 A1 | 3/2014 | Kim et al. | |

FOREIGN PATENT DOCUMENTS

| | | |
|---|---|---|
| WO | 9405224 A1 | 3/1994 |
| WO | 03041596 A1 | 5/2003 |

* cited by examiner

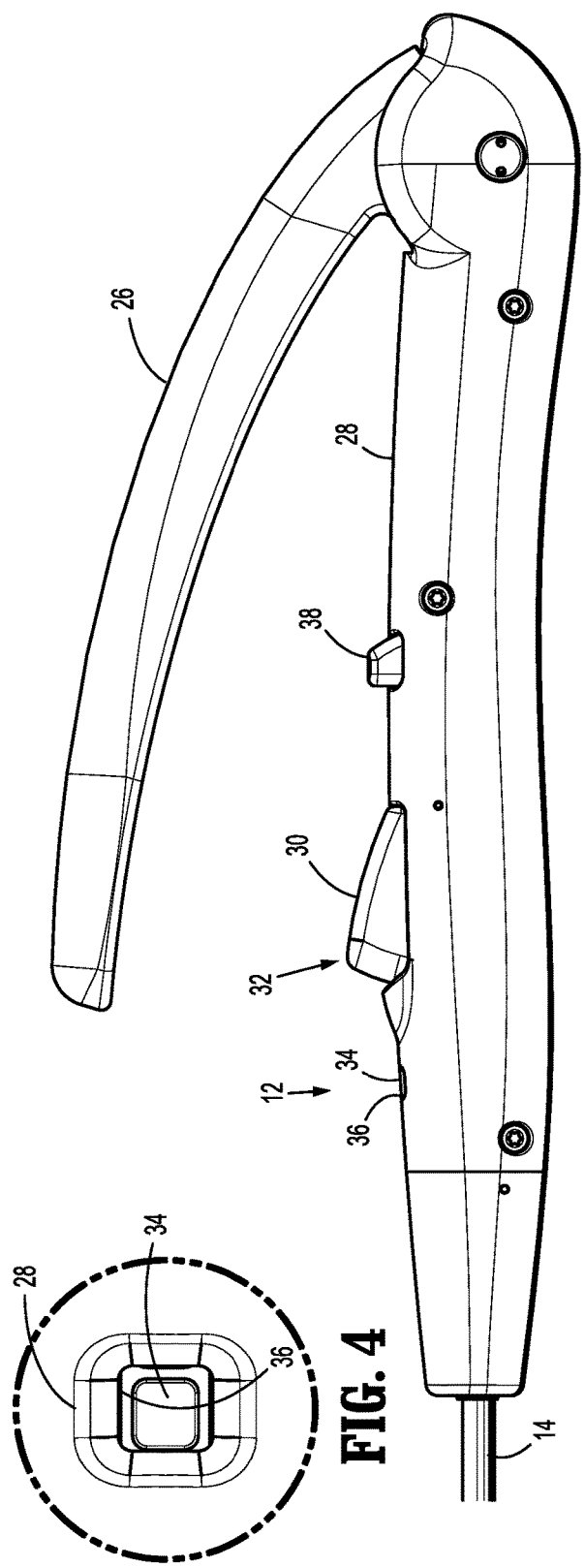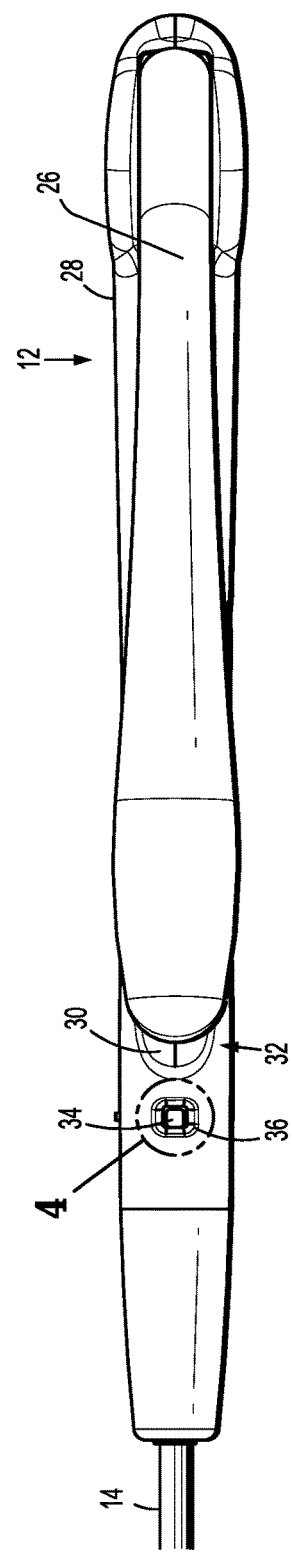

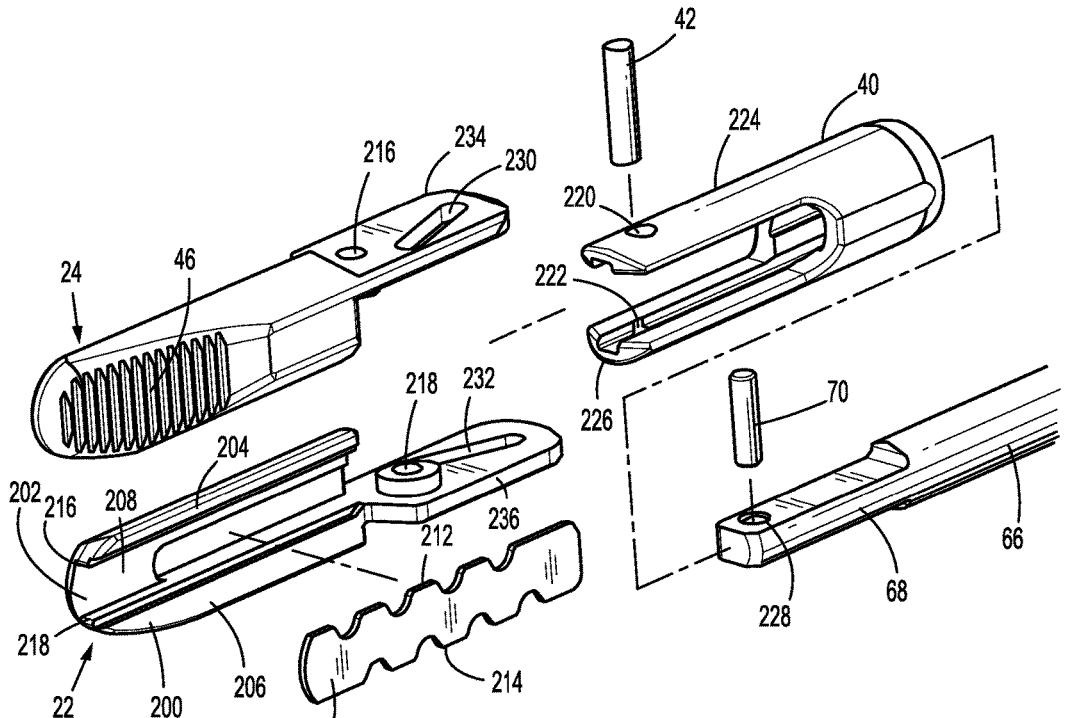
FIG. 9
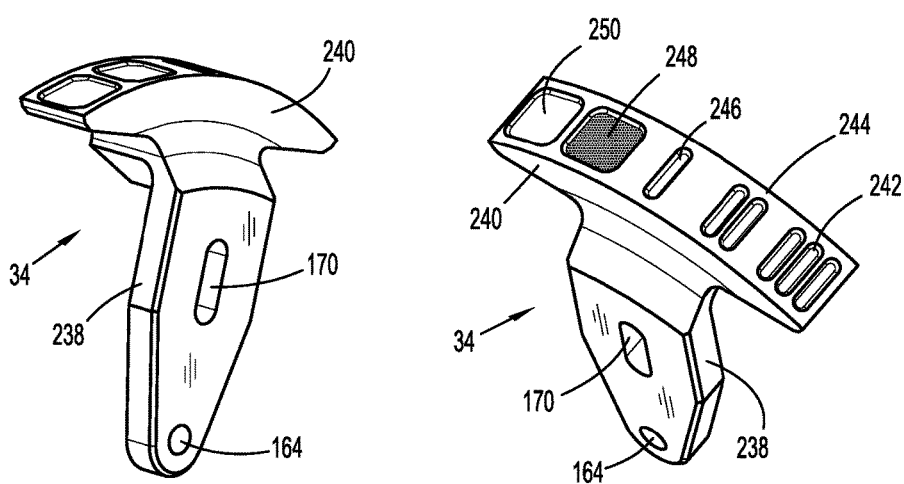
FIG. 10  FIG. 11

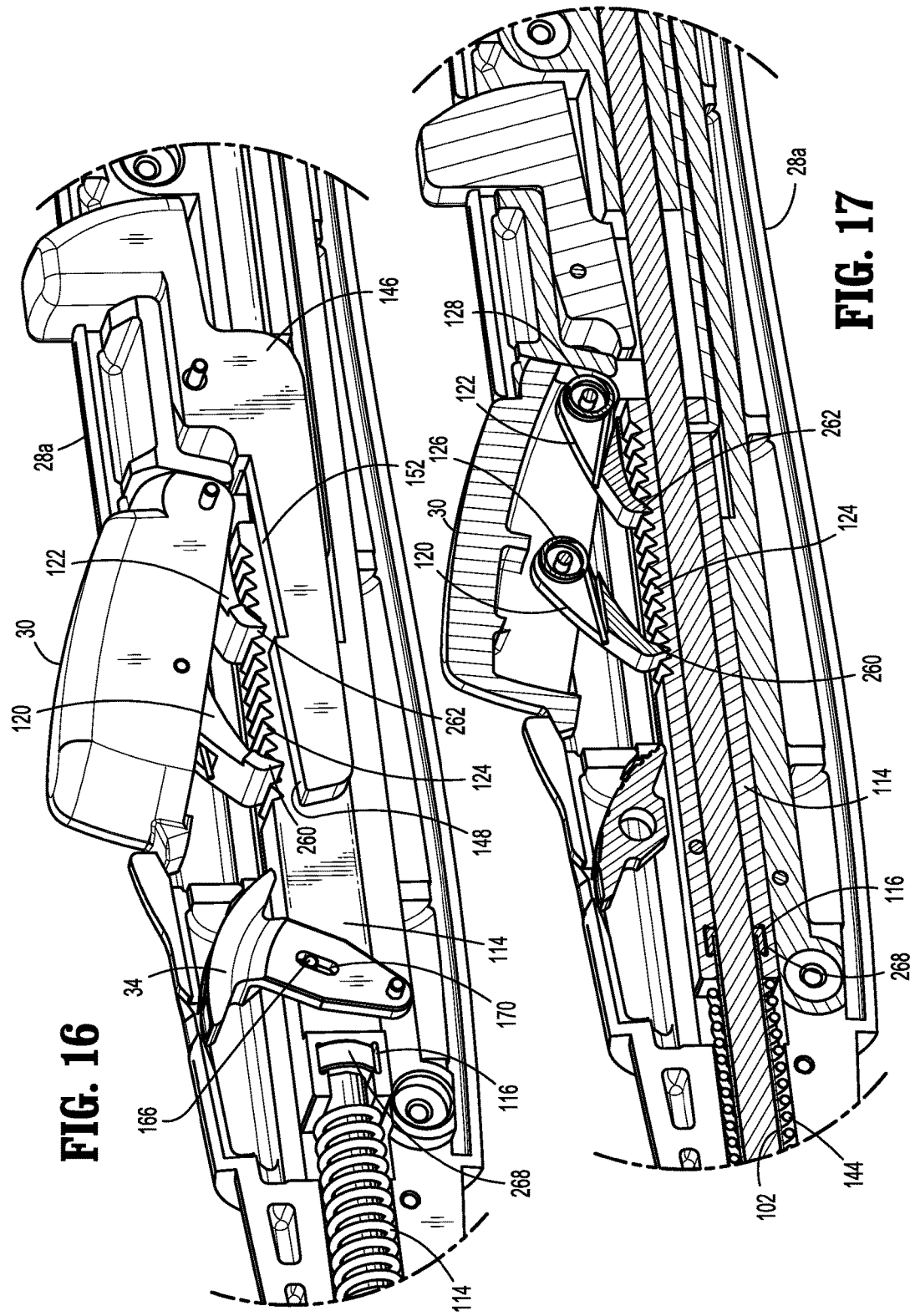

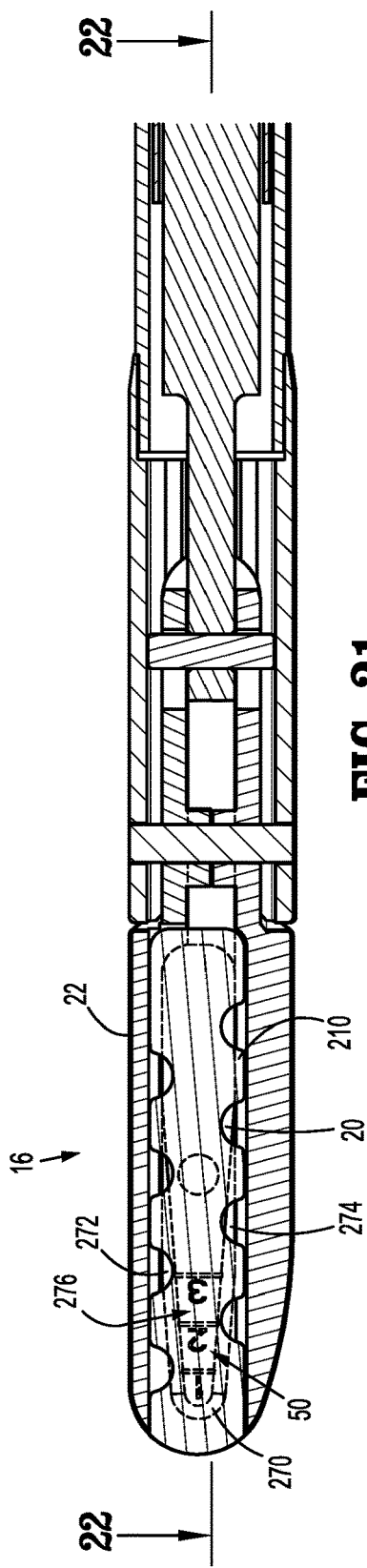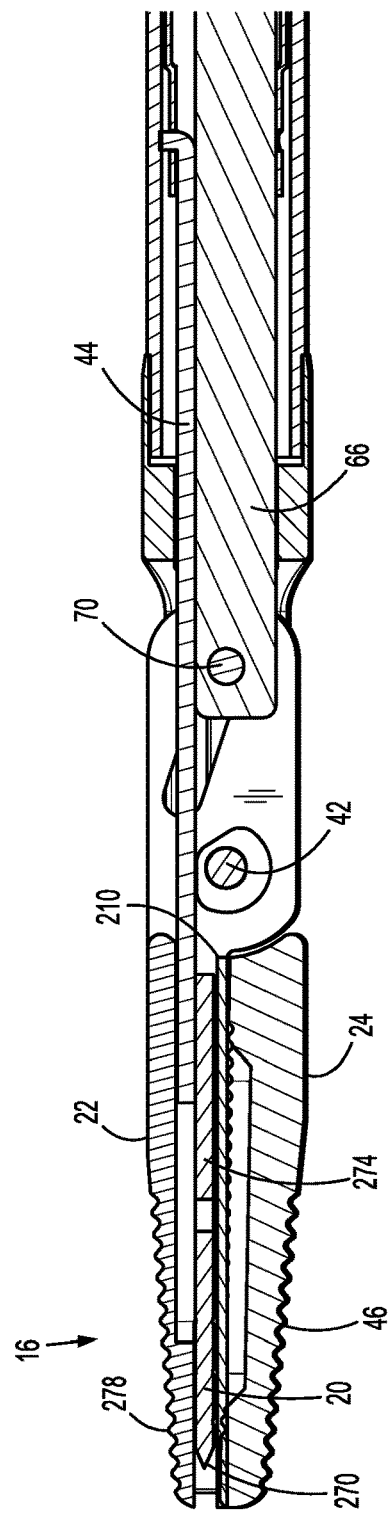

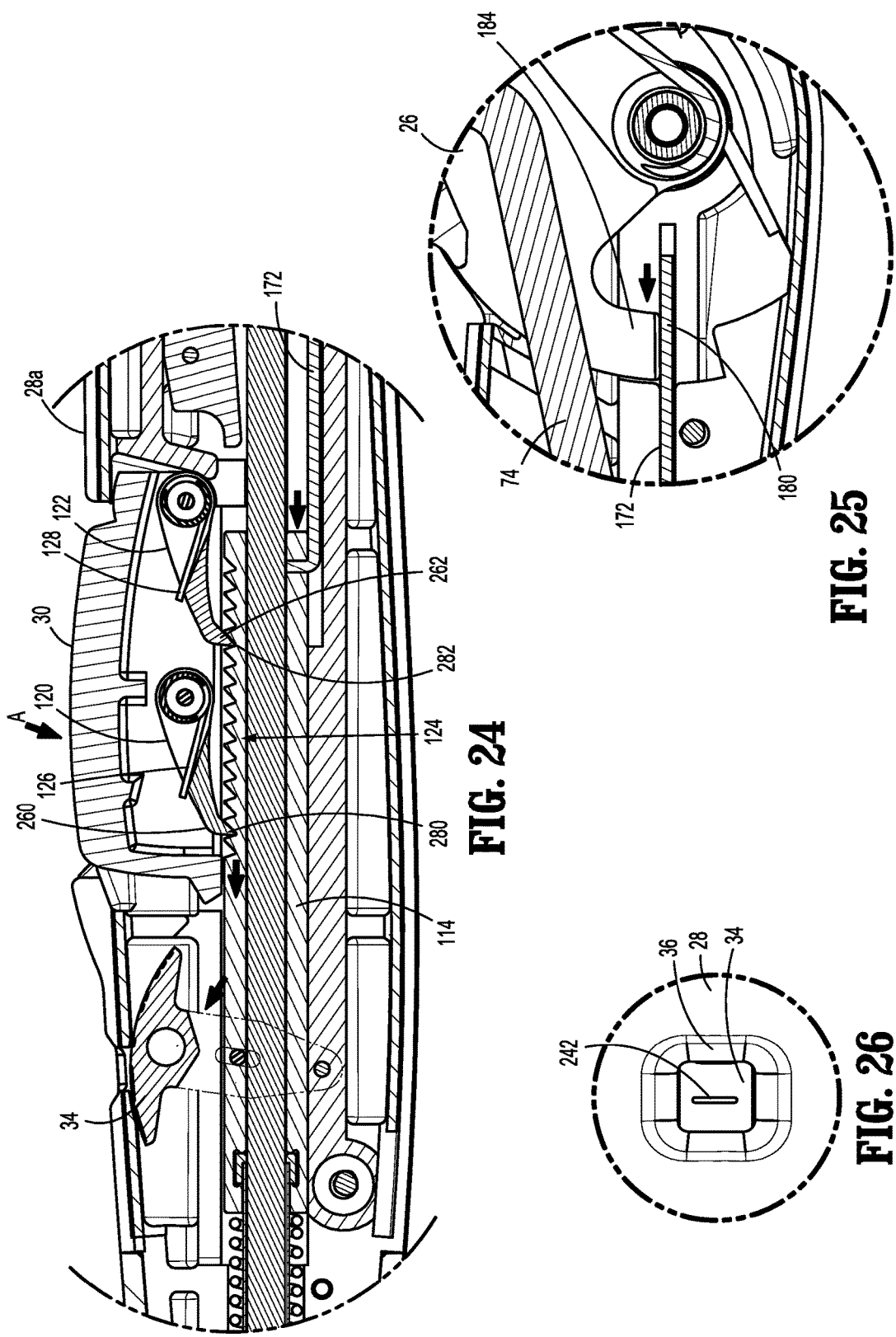

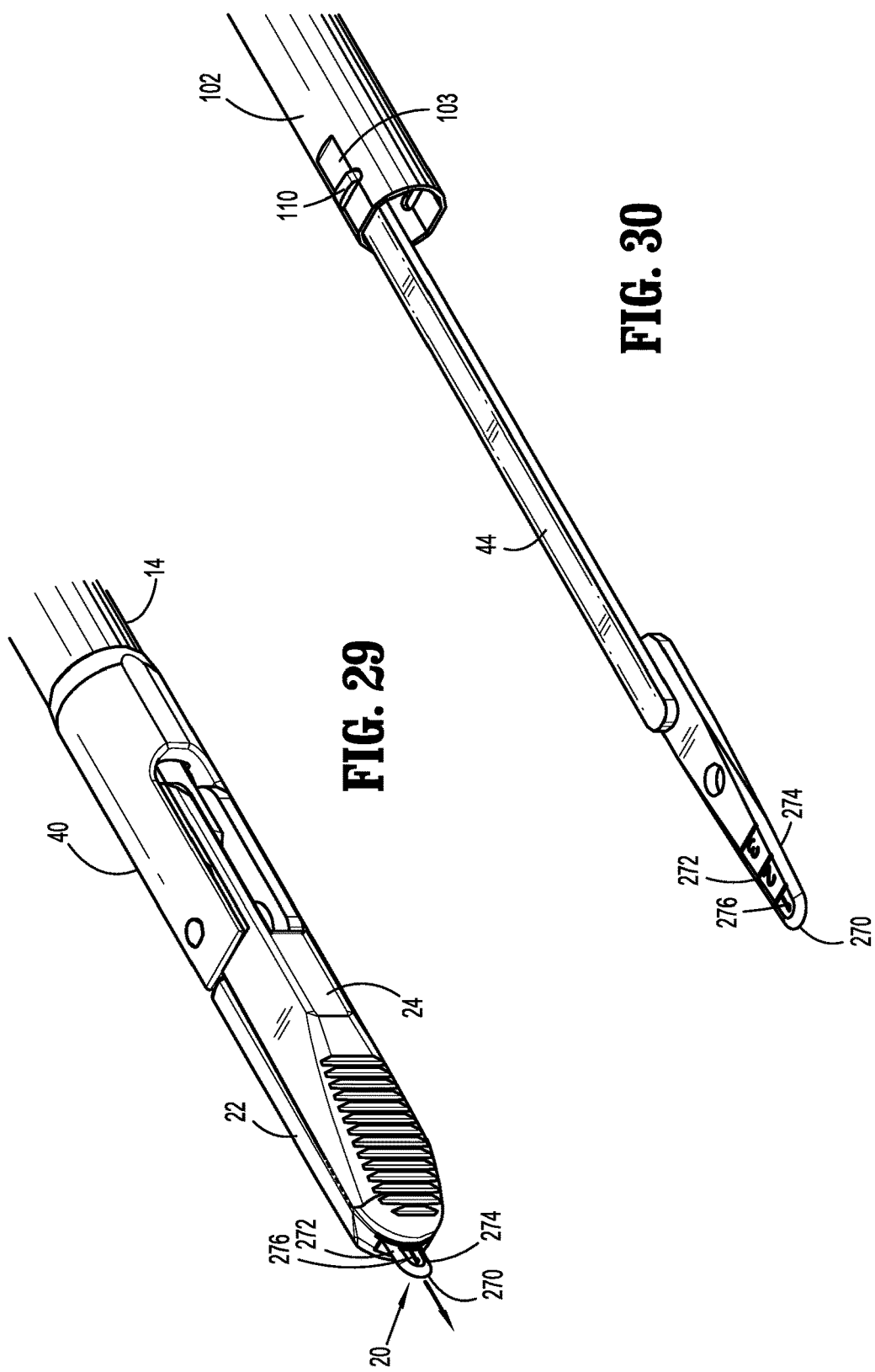

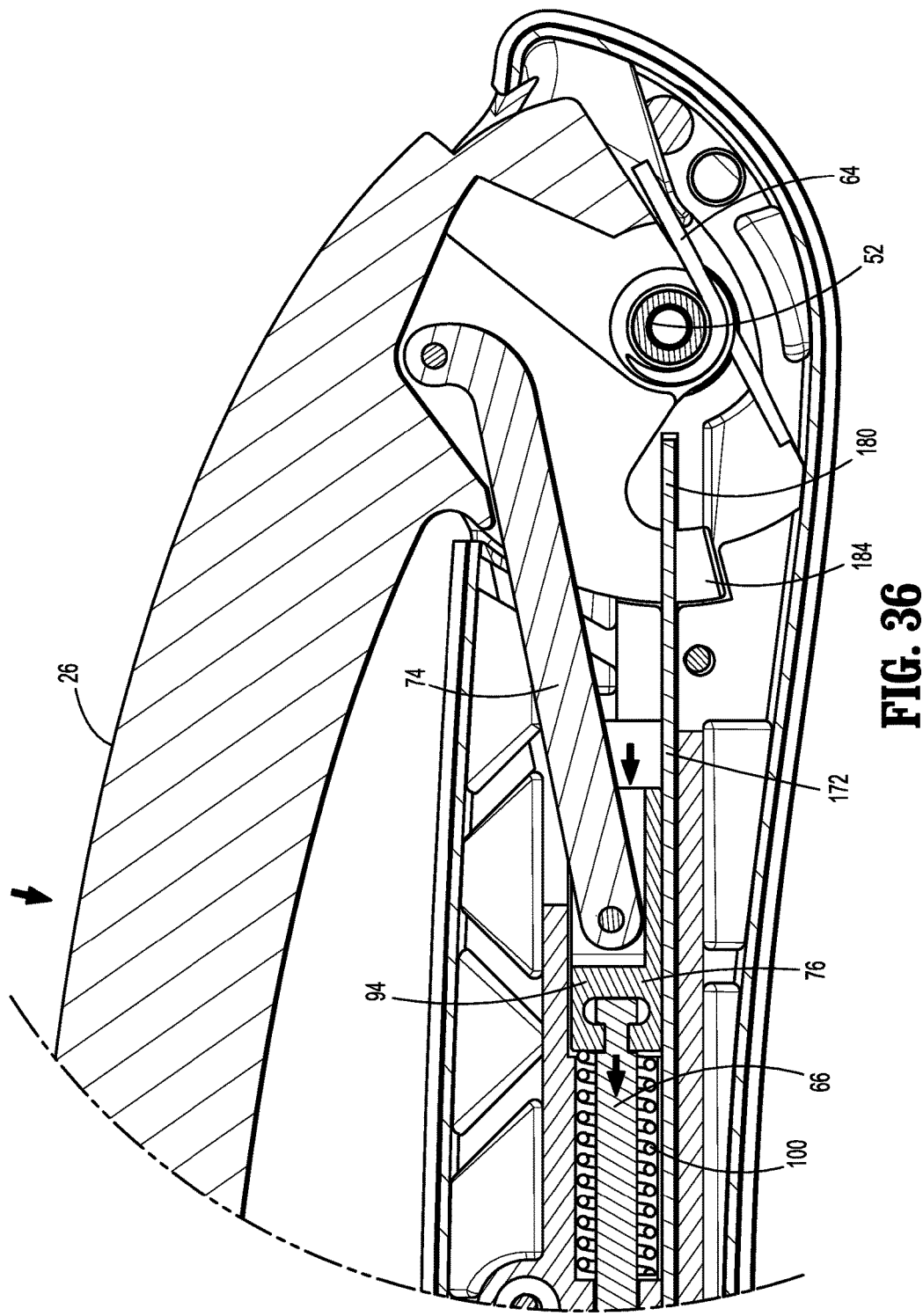

PEDIATRIC COMBINATION SURGICAL DEVICE

CROSS-REFERENCE TO RELATED APPLICATIONS

This application is a continuation of U.S. patent application Ser. No. 14/102,546, filed Dec. 11, 2013, now U.S. Pat. No. 9,439,665, which claims the benefit of and priority to U.S. Provisional Patent Application Ser. No. 61/739,858, filed Dec. 20, 2012, the entire disclosure of each of the above applications is incorporated by reference herein.

BACKGROUND

1. Technical Field

The present disclosure relates to a surgical dissection and grasping device. More particularly, the present disclosure relates to a surgical device having a dissection blade movably mounted within one of a pair of jaws of the surgical device to shield the blade during operation of the jaws.

2. Background of Related Art

Pyloric stenosis is a condition that affects the gastrointestinal tract of infants. It is a thickening and narrowing of the pylorus muscle in the lower part of the stomach where food or other substances pass into the small intestine. It causes vomiting and other complications such as dehydration, salt and fluid imbalances, etc.

Pyloric stenosis is often treated by a surgical procedure called pyloromyotomy which involves severing and spreading the thickened muscle to relax it. This procedure can be performed through open surgery or laparoscopically through a small incision or port. Since the patient is an infant the operative area is very small.

The instruments used in a pyloromyotomy are usually designed with adults in mind and typically included sheathed arthroscopic knives. Other knives in makeshift holders have also been used. These surgical instruments are often too large for the precise cuts needed with infants and, additionally, both graspers and bladed instruments were required thus increasing the number of instruments involved and the time to perform the surgery.

Therefore, there exists a need for a combined dissecting and tissue spreading instrument to limit the number of instruments inserted within the operative cavity of an infant. There further exists a need for a sheathed dissection instrument extendable in discrete, small increments for use on infants. There still further exists a need for a combined surgical instrument having safety mechanisms to prevent extending a dissection blade during use of a pair of spreading jaws or visa versa.

SUMMARY

There is disclosed a surgical device for use in pediatric surgery which generally includes a handle assembly having a handle housing, an elongate tubular member extending distally from the handle assembly and having a distal end, and an end effector assembly mounted on the distal end of the elongate tubular member. The end effector assembly includes a first jaw, a second jaw and a blade movably mounted within the first jaw.

The handle assembly includes an advancement mechanism for extending the blade out of the first jaw. The advancement mechanism is connected to the blade by an intermediate tube or member movably mounted within the elongate tubular member. The advancement mechanism additionally includes a hollow body connected to a proximal end of the intermediate tube and an advance button movably mounted in the handle housing and engageable with the hollow body to drive the hollow body distally within the handle assembly.

An advance pawl is rotatably mounted to the advance button. The hollow body includes ratchet teeth engageable by the advance pawl to incrementally advance the hollow body distally within the handle housing in response to depression of the advance button against the handle housing. The advance button is pivotally mounted on the handle housing at a pivot point and the advancement mechanism further includes a lock pawl engageable with the ratchet teeth and sharing the pivot point with the advance button such that the lock pawl remains engaged with the ratchet teeth upon release of the advance button.

The surgical device further includes a blade retraction lever movably mounted on the handle housing and having a first lift face engageable with the advance pawl and a second lift face engageable with the lock pawl. Actuation of the blade retraction lever lifts the advance pawl and lock pawl out of engagement with the ratchet teeth to free the hollow body for proximal movement to retract the blade within the first jaw.

In an alternate embodiment, the surgical device includes a cam release bar movably mounted within the handle housing and connected to the lever for disengaging the pawls. The cam release bar has a first cam edge engageable with the advance pawl and a second cam edge engageable with the lock pawl such that actuation of the lever drives the cam release bar distally within the housing to lift the advance pawl and lock pawl out of engagement with the ratchet teeth.

The first jaw has a body including a back and first and second sides, the back and first and second sides define a channel for receipt of the blade. The first jaw further includes a retention plate covering the channel to retain the blade within the channel.

There is also disclosed a surgical device for use in pediatric surgery including a handle assembly having a handle housing, an elongate tubular member extending distally from the handle assembly and having a distal end. An end effector assembly is mounted on the distal end of the elongate tubular member. The end effector assembly includes a first jaw, a second jaw movably mounted relative to the first jaw and a blade movably mounted within the first jaw. An advancement mechanism is positioned within the handle housing and operable to extend the blade out of the first jaw. A lever is movably mounted on the handle housing and connected to the first and second jaws. The lever is operable to move the first and second jaws from a closed position in close cooperative alignment to an open position spaced apart to receive tissues.

The lever is connected to the first and second jaws by a center rod which is biased proximally by a compression spring. The compression spring additionally biases the lever to an open position.

A lockout mechanism is provided and is engageable with the advancement mechanism and lever. The lockout mechanism prevents movement of the lever when the blade is in an extended condition out of the first jaw. The lockout mechanism includes a safety bar affixed to the advancement mechanism and having a blocking member positioned adjacent the lever such that the blocking member blocks movement of the lever when the advancement mechanism is in a first position and is remote from the lever when the advancement mechanism is in a second position.

The advancement mechanism includes a ratchet body and the lever includes a depending arm. A distal end of the safety bar is affixed to the ratchet body and a proximal end of the safety bar terminates in a cross-bar for blocking the depending arms of the lever.

The disclosed surgical device additionally includes an indicator on the handle housing and connected to the advancement mechanism. The indicator has markings corresponding to the degree of extension of the blade out of the first jaw. The blade also has indicia corresponding to the degree of extension out of the first jaw.

There is still further disclosed a surgical device for use in pediatric surgery including a handle assembly having a handle housing, an elongate tubular member extending distally from the handle assembly and having a distal end and an end effector assembly mounted on the distal end of the elongate tubular member. The end effector assembly includes a first jaw, a second jaw movably mounted relative to the first jaw and a blade movably mounted within the first jaw. An advancement mechanism is positioned within the handle housing and is operable to extend the blade out of the first jaw. The advancement mechanism including a hollow ratchet body connected to the blade, an advance button mounted to the handle housing and an advance pawl connected to the advance button and engageable with teeth on the hollow ratchet body. A lever is movably mounted on the handle housing and is connected to the first and second jaws. The lever is operable to move the first and second jaws from a closed position in close cooperative alignment to an open position spaced apart to receive tissues. In a particular embodiment, the advancement mechanism includes a lock pawl engageable with the hollow ratchet body.

The surgical device further includes a release member movably mounted in the handle housing and engageable with the advance pawl and the lock pawl. The release member has surfaces disengaging the advance pawl and lock pawl from the hollow ratchet body when the release member is moved from a first position to a second position.

In a specific embodiment, the surgical device includes an electrical connector on the handle housing for supplying cauterizing current to the blade.

DESCRIPTION OF THE DRAWINGS

Various embodiments of the presently disclosed pediatric pyloromyotomy device are disclosed herein with reference to the drawings, wherein:

FIG. 2 is a perspective view of a handle assembly of the pediatric device;

FIG. 3 is a top view of the pediatric device;

FIG. 4 is an enlarged area of detail view of FIG. 3 illustrating an indicator of the pediatric device.

FIG. 9 is a perspective view, with parts separated, of the end effector assembly of the pediatric device;

FIG. 10 is a perspective view of an indicator member of the pediatric device;

FIG. 11 is a further perspective view of the indicator member;

FIG. 16 is an enlarged area of detail view of FIG. 12;

FIG. 17 is an enlarged area of detail view of FIG. 15;

FIG. 21 is an enlarged area of detail view of FIG. 18;

FIG. 22 is a cross sectional view taken along line 22-22 of FIG. 21;

FIG. 24 is an enlarged area of detail view of FIG. 23 illustrating actuation of a blade advancement mechanism;

FIG. 25 is an enlarged area of detail view of FIG. 23 illustrating operation of a handle lockout mechanism;

FIG. 26 is an enlarged view of the indicator;

FIG. 29 is an enlarged perspective view of the end effector with the blade in a deployed condition;

FIG. 30 is a perspective view of the distal end of the pediatric device with components removed to show the blade and a leaf spring connected to the blade;

FIG. 36 is an enlarged area of detail view of FIG. 33 illustrating the lockout mechanism deactivated;

DETAILED DESCRIPTION OF EMBODIMENTS

Embodiments of the presently disclosed pediatric surgical device will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
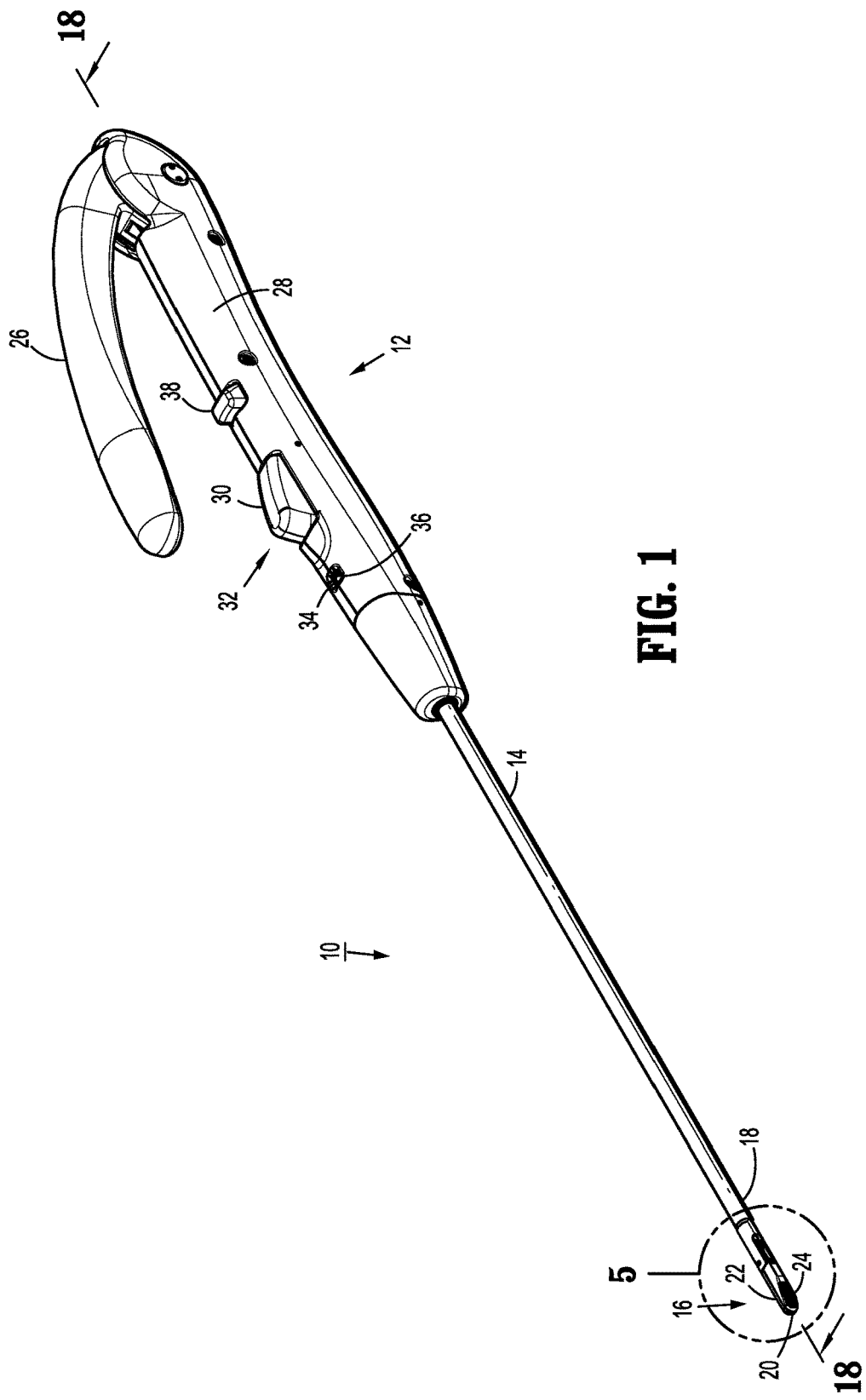
FIG. 1 is a perspective view of one embodiment of a pediatric pyloromyotomy device for use in pediatric surgery.

Referring initially to FIG. 1, there is disclosed one embodiment of a pediatric combination surgical device 10 for use in performing a pyloromyotomy procedure during open or laparoscopic surgery. Surgical device 10 generally includes a handle assembly 12, an elongate tubular member 14 extending distally form handle assembly 12 and an end effector assembly 16 mounted on a distal end 18 of elongate tubular member 14. In a specific embodiment, elongate tubular member 14 has an outer diameter of 3 mm making it particularly suitable for use in pediatric surgery.

End effector assembly 16 combines multiple functions such as, for example, cutting, dissecting, grasping, spreading, etc. and includes a blade 20 movably mounted in a first jaw 22. A second jaw 24 is movably mounted relative to first jaw 22 to grasp and spread tissue. Handle assembly 12 includes a lever 26 movably mounted to a handle housing 28 of handle assembly 12. Lever 26 is operable to move first and second jaws 22 and 24 relative to each other to grasp and spread tissue.

Referring now to FIGS. 1-3, In order to extend blade 20 out of first jaw 22, handle assembly 12 includes an advance button 30 which is part of an advancement mechanism 32 and functions to incrementally advance blade 20 out of first jaw 22 in a manner described in more detail hereinbelow. An indicator 34 is provided to give a visual indication of the extent of the extension of blade 20 out of first jaw 22 and is visible through a window 36 provided in handle housing 28 (FIG. 4). Finally, a retract button 38 (FIGS. 1 and 2) is provided in handle assembly 12 and is operable to disengage advancement mechanism 32 and allow blade 20 to retract fully within first jaw 22.

Figure 5:
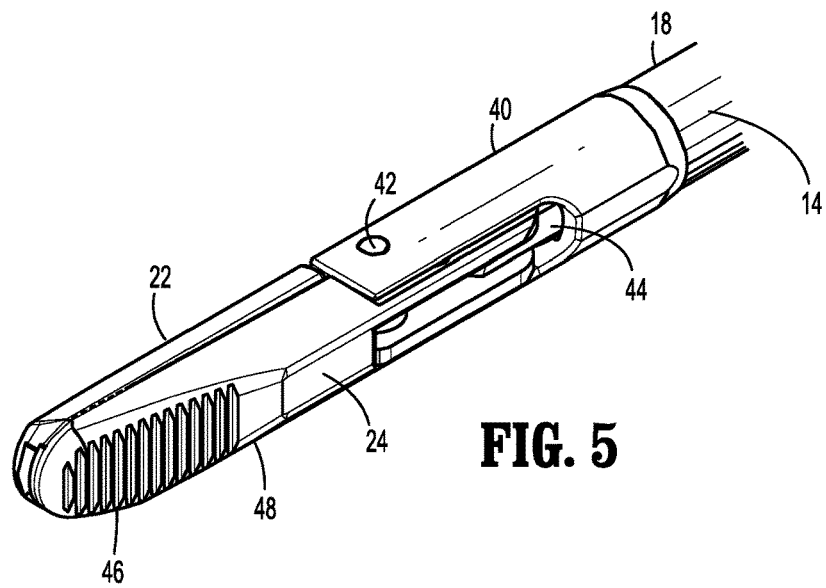
FIG. 5 is a perspective view of the distal end of the pediatric device illustrating an end effector assembly.
Figure 6:
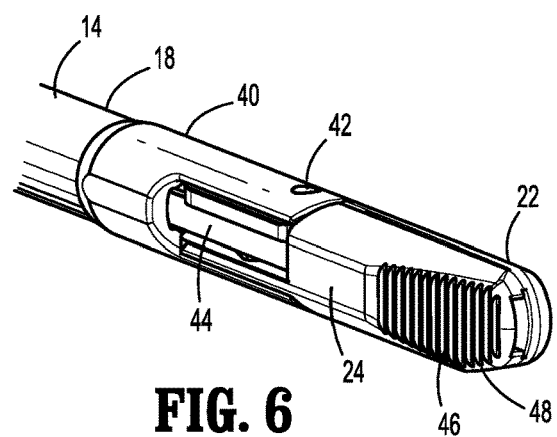
FIG. 6 is a further perspective view of the distal end of the pediatric device similar to FIG. 5.
Figure 7:
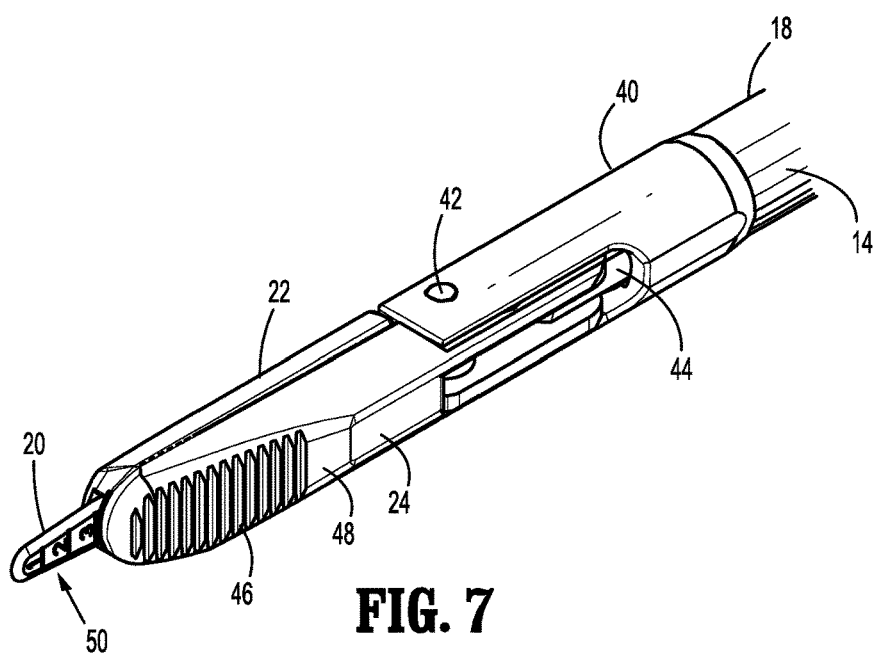
FIG. 7 is a perspective view of the distal end of the pediatric device with a blade of the end effector assembly in a deployed position.

Referring to FIGS. 5-7, first and second jaws 22 and 24 are pivotally mounted on a clevis 40 affixed to distal end 18 of elongate tubular member 14 by a pivot pin 42. An elastic leaf spring 44 extends through elongate tubular member 14 and clevis 40 and is provided to operate blade 20. As shown, second jaw 24 includes serrations 46 on a tapered outer surface 48 to facilitate engagement with tissue when used to spread tissue.

With specific reference to FIG. 7, blade 20 includes indicator markings 50, such as for example 1, 2, 3, etc., to indicate the extent of extension of blade 20 out of first jaw 22 and correspond to similar markings provided on indicator 34 (see FIGS. 10 and 11). Indicator markings 50 are formed by laser etching or other means of permanent marking such as, for example, photo etching, engraving, etc.

Figure 8:
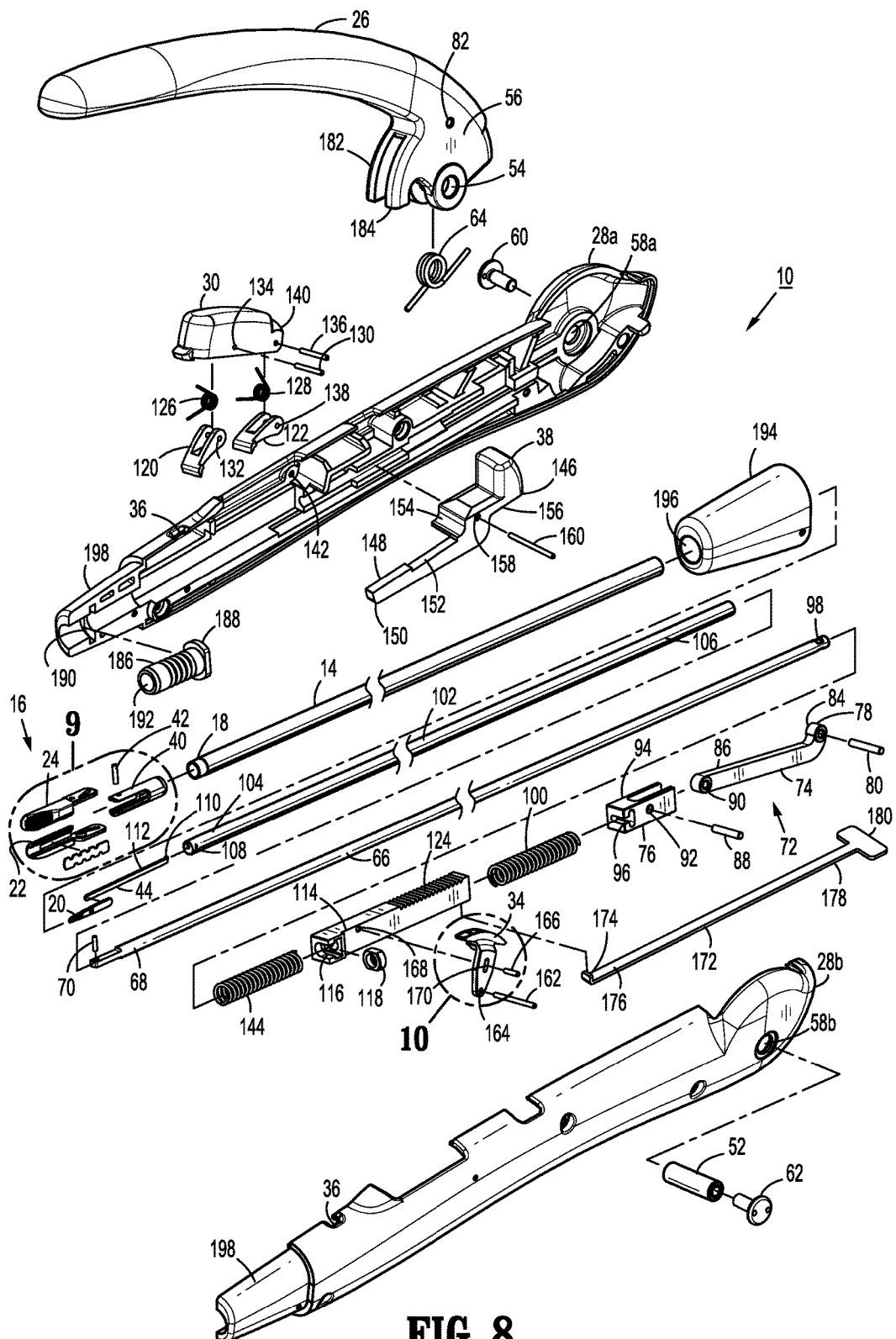
FIG. 8 is a perspective view, with parts separated, of the handle assembly of the pediatric device.

Turning now to FIG. 8, handle housing 28 of handle assembly 12 of surgical device 10 is formed as two complimentary halves 28a and 28b and are joined by welding, gluing, snap fit, etc. As noted hereinabove, lever 26 is operable to move first and second jaws 22 and 24 from a closed condition adjacent each other to an open position spaced apart. Lever 26 is pivotally connected to handle housing 28 by a pivot shaft 52 extending through a bore 54 formed in a base 56 of lever 26. Pivot shaft 52 extends through holes 58a and 58b formed in handle housing halves 28a and 28b, respectively. End caps 60 and 62 are press fit into pivot shaft 52 to secure pivot shaft 52 to handle housing 28. Lever 26 is biased to an open position by a torsion spring 64 mounted in handle housing 28.

In order to move first and second jaws 22 and 24, a center rod 66 is provided and extends through elongate tubular member 14. A distal end 68 of center rod 66 is connected to first and second jaws 22 and 24 by a drive pin 70. Longitudinal movement of center rod 66 within outer tubular member 14 moves first and second jaws 22 and 24 between the closed and open positions. Lever 26 is connected to center rod 66 by a linkage assembly 72 including a drive link 74 and a slider 76. A proximal end 78 of drive link 74 is connected to lever 26 by a pin 80 extending through a hole 82 in base 56 of lever 26 and a hole 84 extending through proximal end 78 of drive link 74. A distal end 86 of drive link 74 is connected to slider 76 by a second pin 88 extending through a hole 90 in distal end 86 and a hole 92 in slider 76. A distal end 94 of slider 76 includes a slot 96 which receives a flanged proximal end 98 of center rod 66. A compression spring 100 is provided within handle housing 28 and engages and biases slider 76 proximally within handle housing 28. Movement of lever 26 toward handle housing 28 drives drive link 74 and slider 76 distally within handle housing 28 and thus center rod 66 distally within elongate tubular member 14 to move first and second jaws 22 and 24 to the open position. Compression spring 100 biases slider 76 proximally and torsion spring 64 biases lever 26 to an open position to maintain first and second jaws 22 and 24 in the closed position.

In order to move blade 20 between the extended and retracted positions in first jaw 22, surgical device 10 includes an intermediate tube 102 having a distal end 104 and a proximal end 106. A slot 108 in distal end 104 of intermediate tube 102 is provided to receive a tab 110 at a proximal end 112 of elastic leaf spring 44. Advancement mechanism 32 includes a hollow ratchet body 114 which is longitudinally mounted in handle housing 28 and includes a distal slot 116 for receipt of proximal end 106 of intermediate tube 102. A cam collar 118 secures proximal end 106 of intermediate tube 102 within distal slot 116 of hollow ratchet body 114.

Advancement mechanism 32 additionally includes an advance pawl 120 and a lock pawl 122 which are configured to engage ratchet teeth 124 provided on hollow ratchet body 114 and move hollow ratchet body 114 distally to extend blade 20 and lock it in position for use. First and second torsion springs 126 and 128 are provided between advance button 30 and advance pawl 120 and lock pawl 122 to bias the pawls into engagement with ratchet teeth 124 on hollow ratchet body 114. Advance pawl 120 is pivotally mounted to advance button 30 by a first pin 130 extending through holes 132 in advance pawl 120 and holes 134 in advance button 30. First pin 130 also supports first torsion spring 126. Likewise, a second pin 136 extends through holes 138 in lock pawl 122 and holes 140 in advance button 30. Additionally, second pin 136 serves to pivotally mount advance button 30 on handle housing 28 and is mounted within supports 142 in handle housing halves 28a and 28b. Thus, advance button 30 and lock pawl 122 have a common pivot point allowing lock pawl 122 to remain engaged with hollow ratchet body 114 until disengaged as described below.

Hollow ratchet body 114 is biased proximally within handle housing 28 by a compression spring 144 to maintain blade 20 in a retracted position within first jaw 22 (FIG. 5).

As noted above, advancement mechanism 32 is used to advance blade 20 out of first jaw 22 and lock it in the extended position. In order to unlock and retract blade 20, surgical device 10 includes a blade retraction lever 146 having a distal lift face 148 at a distal end 150 of retraction lever 146 and an intermediate lift face 152 proximal of distal lift face 148. Intermediate lift face 152 extends distally from a center body 154 of retraction lever 146 and retraction button 38 is integral with a proximal end 156 of retraction lever 146. Retraction lever 146 includes a hole 158 in center body 154 and pivots about a pivot pin 160 extending through hole 158. Pivot pin 160 rotationally supports retraction lever 146 within handle housing 28. Depression of retract button 38 pivots retraction lever 146 to drive distal and intermediate lift faces 148, 152 upward into engagement with advance and lock pawls 120, 122, respectively, to allow blade 20 to retract within first jaw 22.

Indicator 34 is provided to give a visual indication of the degree of extension of blade 20 out of first jaw 22. Indicator 34 is pivotally connected to handle housing 28 by a pivot pin 162 which extends through a hole 164 in indicator 34. A drive pin 166 is affixed within a hole 168 in hollow ratchet body 114 and rides within a slot 170 formed in indicator 34. As hollow ratchet body 114 is advanced, indicator 34 is rotated about pivot pin 162 to display blade 20's position relative to first jaw 22.

In order to prevent first and second jaws 22 and 24 from being opened while blade 20 is in the extended position, surgical device 10 includes a lock out mechanism or safety lock bar 172 which blocks lever 26 from movement when hollow ratchet body 114 is not in the fully retracted position holding blade 20 completely within first jaw 22. Safety lock bar 172 includes a tab 174 at a distal end 176 which is affixed to hollow ratchet body 114. A proximal end 178 of safety lock bar 172 includes a T-shaped bar 180 which blocks movement of a pair of arms 182 and 184 extending from base 56 of lever 26 thereby preventing movement of lever 26.

As shown, surgical device 10 additionally includes a guide sleeve 186 having a proximal flange 188 which is supported in slots 190 formed in handle housing halves 28a and 28b. Guide sleeve 186 has a hollow bore 192 for support and passage of elongate tubular member 14. Additionally, a conical end piece 194 having an opening 196 is affixed over an outer surface 198 of handle housing halves 28a and 28b to assist in holding them together. Elongate tubular member 14 passes through opening 196. In one embodiment, conical end piece 194 may be affixed to outer tubular member 14 and rotate relative to handle housing 28 to rotate and orient end effector assembly 16 relative to tissue.

Turning now to FIG. 9, first jaw 22 includes a hollow body portion 200 for receipt of blade 20. Hollow body portion 200 includes a back 202 and first and second sides 204, 206 defining a channel 208 for receipt of blade 20. A retention or cover plate 210 having scalloped edges 212 and 214 is provided to fit over channel 208 to maintain blade 20 within channel 208. Scalloped edges 212 and 214 fit into longitudinal edges or ledges 216 and 218 formed along first and second sides 204 and 206 of hollow body portion 200. Cover plate 210 may be attached to hollow body portion 200 by snap or press fit or can be permanently affixed by various methods such as, for example, welding, gluing, etc. or may be formed integrally with hollow body portion 200.

First and second jaws 22 and 24 pivot about pivot pin 42. Pivot pin 42 extends through pivot holes 216, 218 in first and second jaws 22 and 24 and is mounted through holes 220,222 formed in longitudinally extending arms 224,226 of clevis 40. Similarly, drive pin 70 is mounted through a hole 228 formed through distal end 68 of center rod 66. Drive pin 70 rides within angled slots 230, 232 formed in proximal plates 234 and 236 of first and second jaws 22 and 24, respectively. Thus, longitudinal movement of center rod 66 cams first and second jaws 22 and 24 about pivot pin 42 between open and closed positions.

Referring now to FIGS. 8, 10 and 11, indicator 34 includes a lever arm 238 and an arcuate head 240. Lever arm 238 includes pivot hole 164 for mounting indicator 34 on pivot pin 162 and is formed with slot 170 for receipt of drive pin 166 (FIG. 8). Arcuate head 240 includes blade position indicia such as, for example position indicia 242, 244 and 246. As ratchet body 114 moves distally to extend blade 20, indicator 34 is rotated counter clockwise such that indicia 242, 244 and 246 become progressively visible through window 36 in handle housing 28. India 242 indicates full extension of blade 20 while indicia 244 and 246 indicate lesser degrees of partial extension of blade 20. In these three positions, blade 20 is extended and lever 26 is blocked from movement by safety lock bar 172. Arcuate head 240 is additionally provided with first and second safety indicia 248 and 250. First safety indicia 248 corresponds to a state where blade 20 is retracted but lever 26 is still blocked from movement by safety lock bar 172. Second safety indicia 250 corresponds to the condition wherein hollow ratchet body 114 is in a proximal most position and lever 26 is not blocked by safety lock bar 172 and is thus free to move jaws 22,24 between the open and closed positions.

Figure 12:
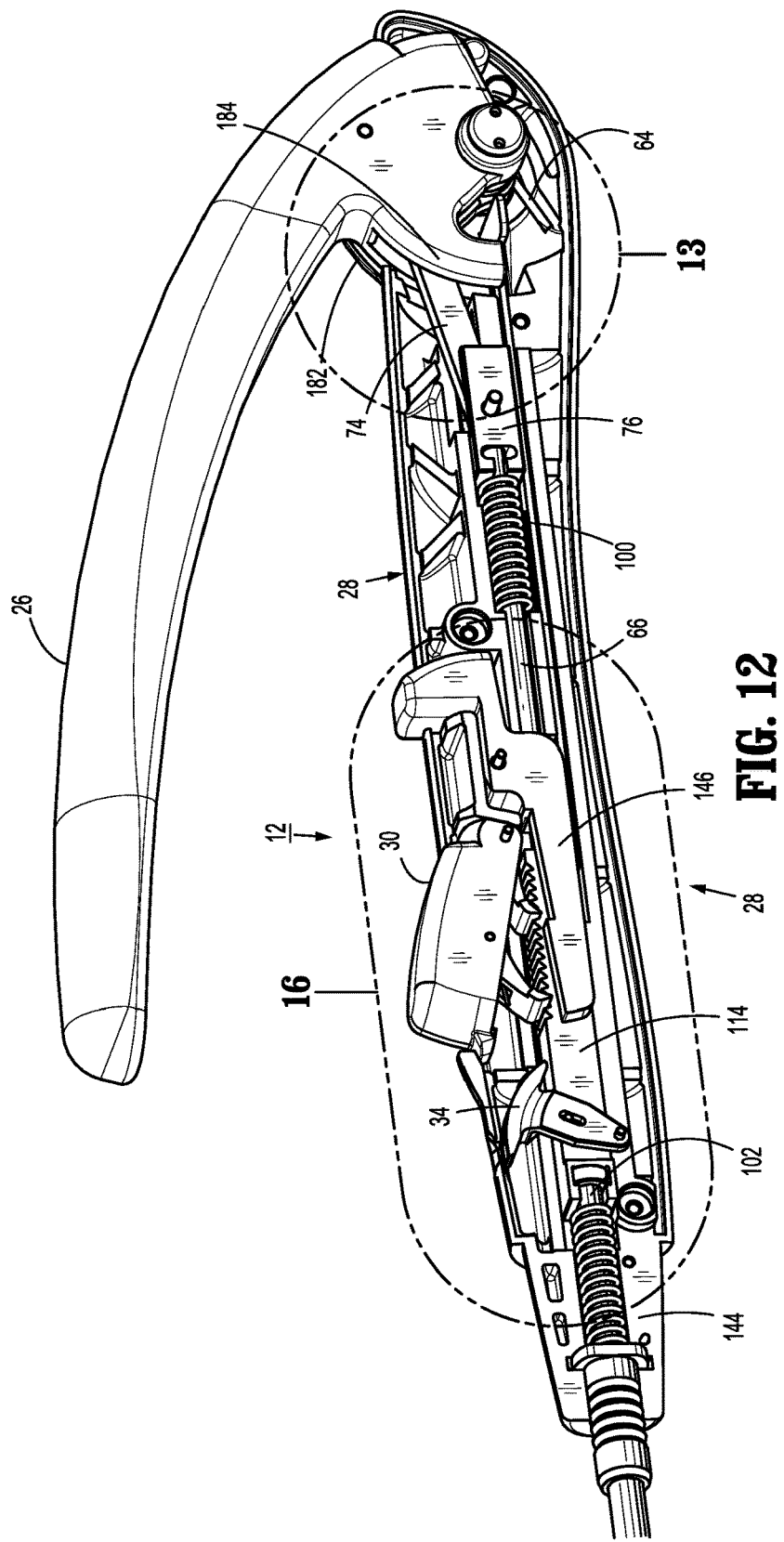
FIG. 12 is a perspective view, with half of a handle housing removed, of the handle assembly of the pediatric device.

Turning now to FIGS. 12-37, and initially with regard to FIGS. 12-14, the operation of surgical device 10 will now be described. With reference to FIG. 12, lever 26 is in the open position against the bias of compression spring 100 and torsion spring 64. Hollow ratchet body 114 is in a proximal most position retaining blade 20 within first jaw 22 (FIG. 21). Advance button 30 is in the upper most position and available to advance blade 20. Indicator 34 is positioned such that second safety indicia 250 is visible through window 36 in handle housing 28. In the proximal most position, hollow ratchet body 114 maintains safety lock bar 172 in a proximal most position allowing for actuation of lever 26 to open and close first and second jaws 22 and 24.

Figure 13:
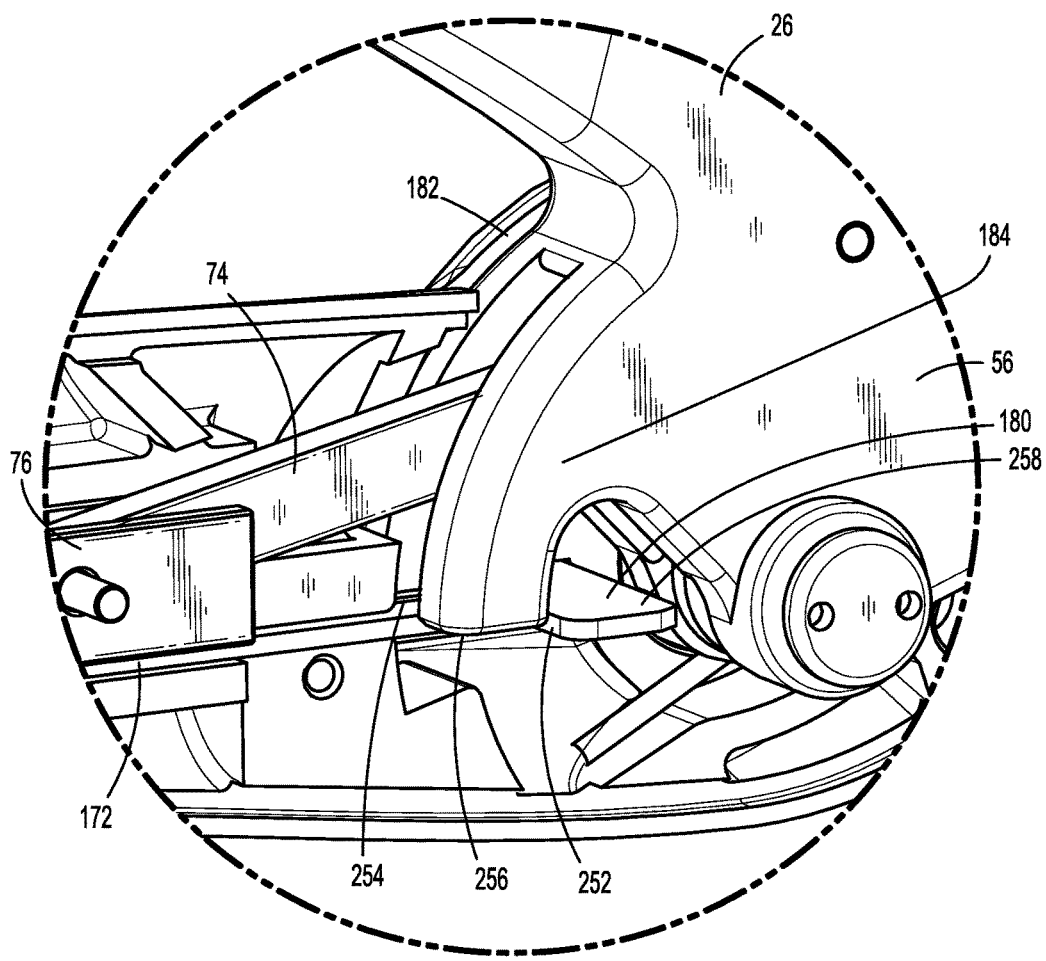
FIG. 13 is an enlarged area of detail view of FIG. 12.
Figure 14:
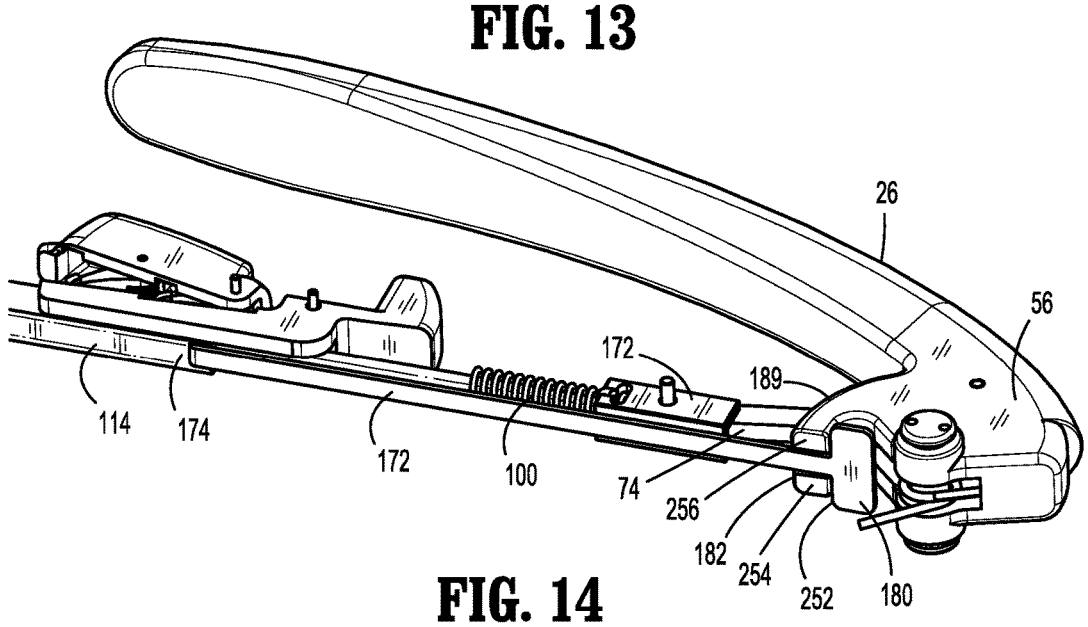
FIG. 14 is a perspective view of handle components of the handle assembly of the pediatric device illustrating a safety lock bar.

Referring for the moment specifically to FIGS. 13 and 14, in the initial position, a leading edge of bar 180 of safety lock bar 172 is proximal to arms 182 and 184 of lever 26 and end faces 254 and 256 of arms 182, 184, respectively, are not blocked by an upper surface 258 of bar 180. Safety lock bar 172 is maintained in the proximal position by hollow ratchet body 114 through engagement of tab 174 of safety lock bar 172 with hollow ratchet body 114 (FIG. 14). Thus, the entire surgical device is free for operation and not "locked out".

Figure 15:
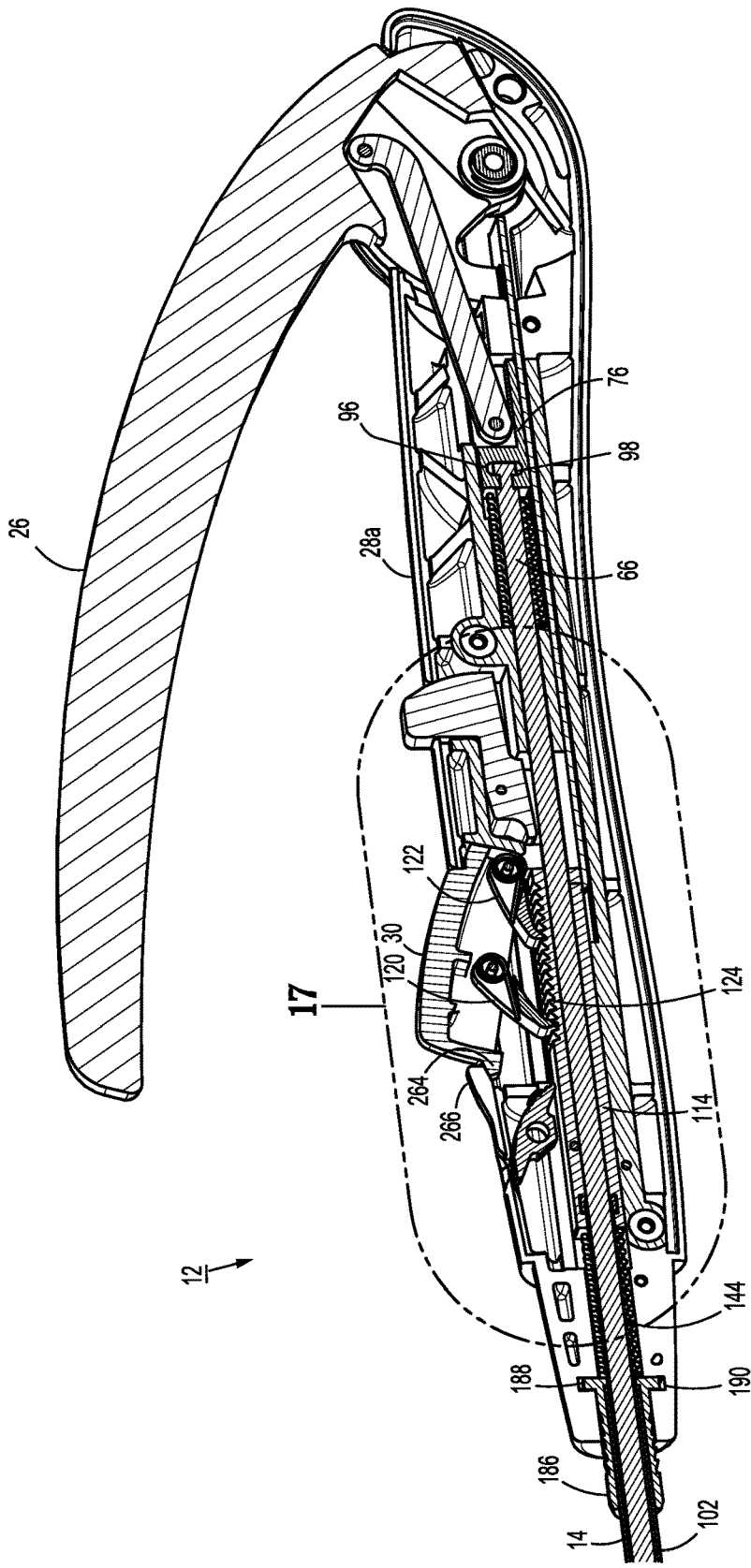
FIG. 15 is a perspective view, partially shown in section, of the handle assembly of the pediatric device.
Figure 18:
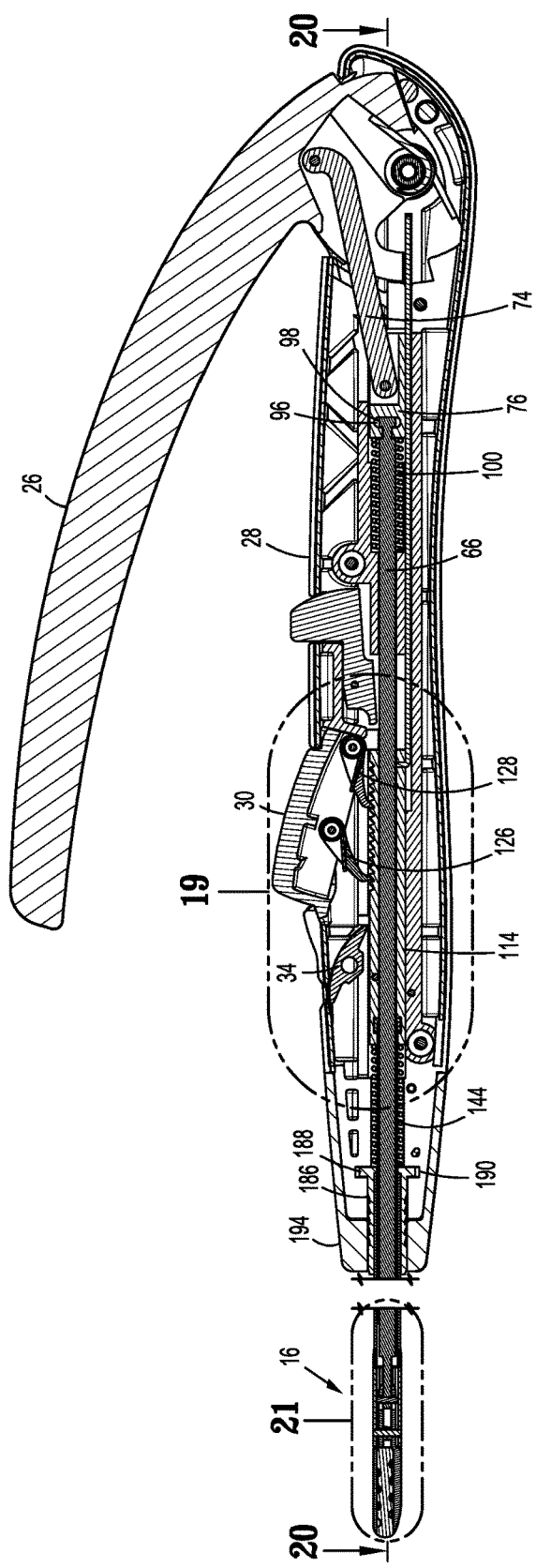
FIG. 18 is a side view, shown in section, of the pediatric device of FIG. 1.
Figure 19:
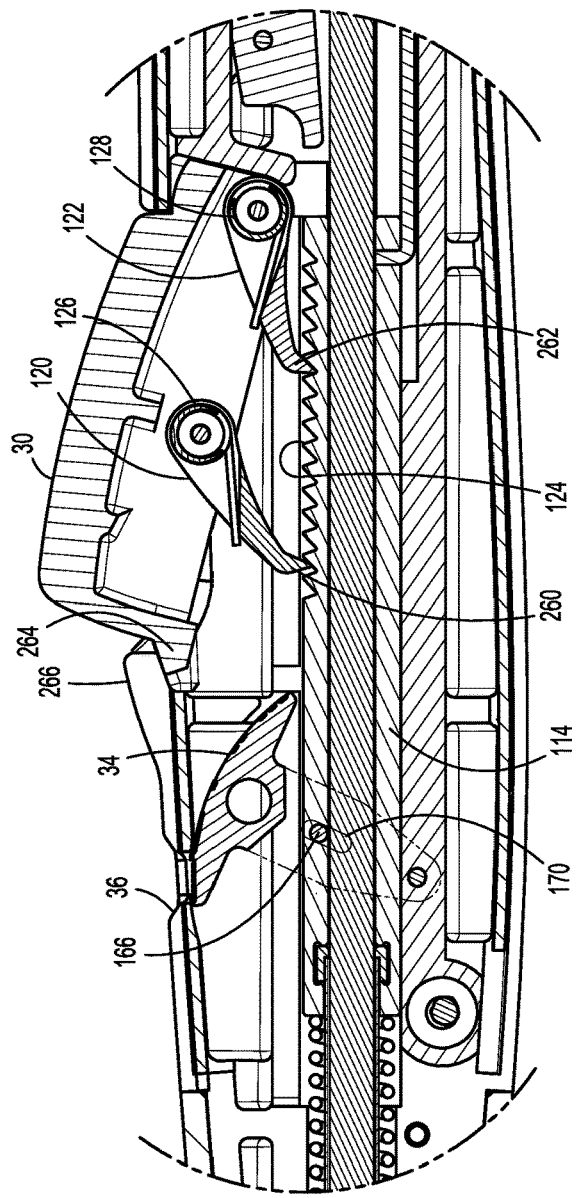
FIG. 19 is an enlarged area of detail view of FIG. 18 illustrating a blade advance mechanism of the pediatric device.

Referring now to FIGS. 15-19, in the initial position, advance button 30 is in the upper position with advance pawl 120 and lock pawl 122 resting on ratchet teeth 124 of hollow ratchet body 114. Hollow ratchet body 114 and intermediate tube 102 (and thus blade 20) are maintained in the proximal position by compression spring 144 (see also FIG. 20). As best shown in FIGS. 15 and 19, drive pin 166 in hollow ratchet body 114 lies within drive slot 170 of indicator 34 and maintains indicator 34 in the initial position indicating both advance button 30 and lever 26 are free to move. Advance button 30 includes a distal lip 264 which engages a housing edge 266 to prevent advance button 30 from lifting out of handle housing 28.

With specific reference to FIGS. 16 and 17, advance pawl 120 and lock pawl 122 include respective engagement teeth 260 and 262 which rest on ratchet teeth 124 of hollow ratchet body 114. Engagement teeth 260 and 262 are biased into engagement with ratchet teeth 124 by respective first and second torsion springs 126 and 128 (FIG. 17). Additionally, first and second torsion springs 126 and 126 bias and maintain upward pressure on advance button 30 (FIG. 18).

Figure 20:
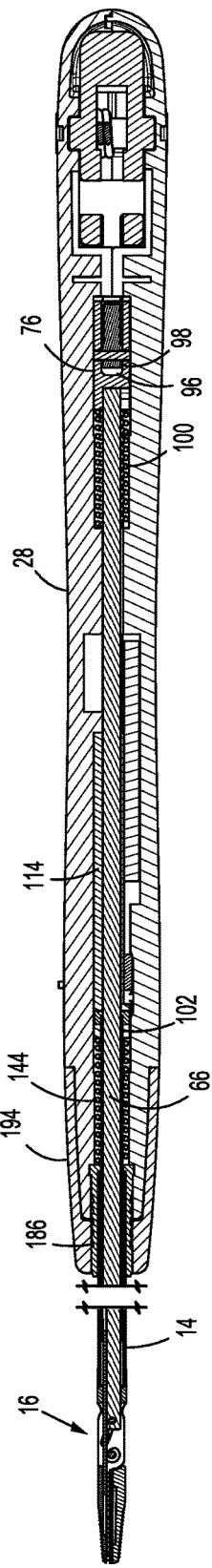
FIG. 20 is a cross sectional view taken along line 20-20 of FIG. 1.

As noted herein above, end effector assembly 16 is rotatable relative to handle housing 28 about the long axis of elongate tubular member 14 by manipulation of conical end piece 194. To accomplish this, guide sleeve 186 is affixed to elongate tubular member 14 and flange 188 of guide sleeve 186 is journeled or rotatably mounted within slots 190 in handle housing halves 28a and 28b (FIGS. 15 and 18). Conical end piece 194 is affixed to guide sleeve 186 (FIGS. 18 and 20). Proximal end 98 of enter rod 66 is rotatably mounted in slot 96 of slider 76 (FIGS. 15, 18 and 20) allowing first and second jaws 22 and 24 to rotate with elongate tubular member 14. Likewise, as best shown in FIGS. 16 and 17, proximal end 106 of intermediate tube 102 includes cam collar 118 or rotatable end collar 268 which is rotatably mounted within distal slot 116 of hollow ratchet body 114. Thus, blade 20 is free to rotate with first jaw 22 (FIG. 21)

Referring now to FIGS. 21 and 22, blade 20 includes a sharp, radiused distal dissecting tip 270 and side cutting edges 272 and 274. As best shown in FIG. 21, indicator markings 50 are in the form of numerical indicia 276 on blade 20 and are visible when blade 20 is extended out of first jaw 22. As shown in FIG. 22, first jaw 22 includes serrations 278 similar to serrations 46 on second jaw 24 to assist in spreading tissue.

Figure 23:
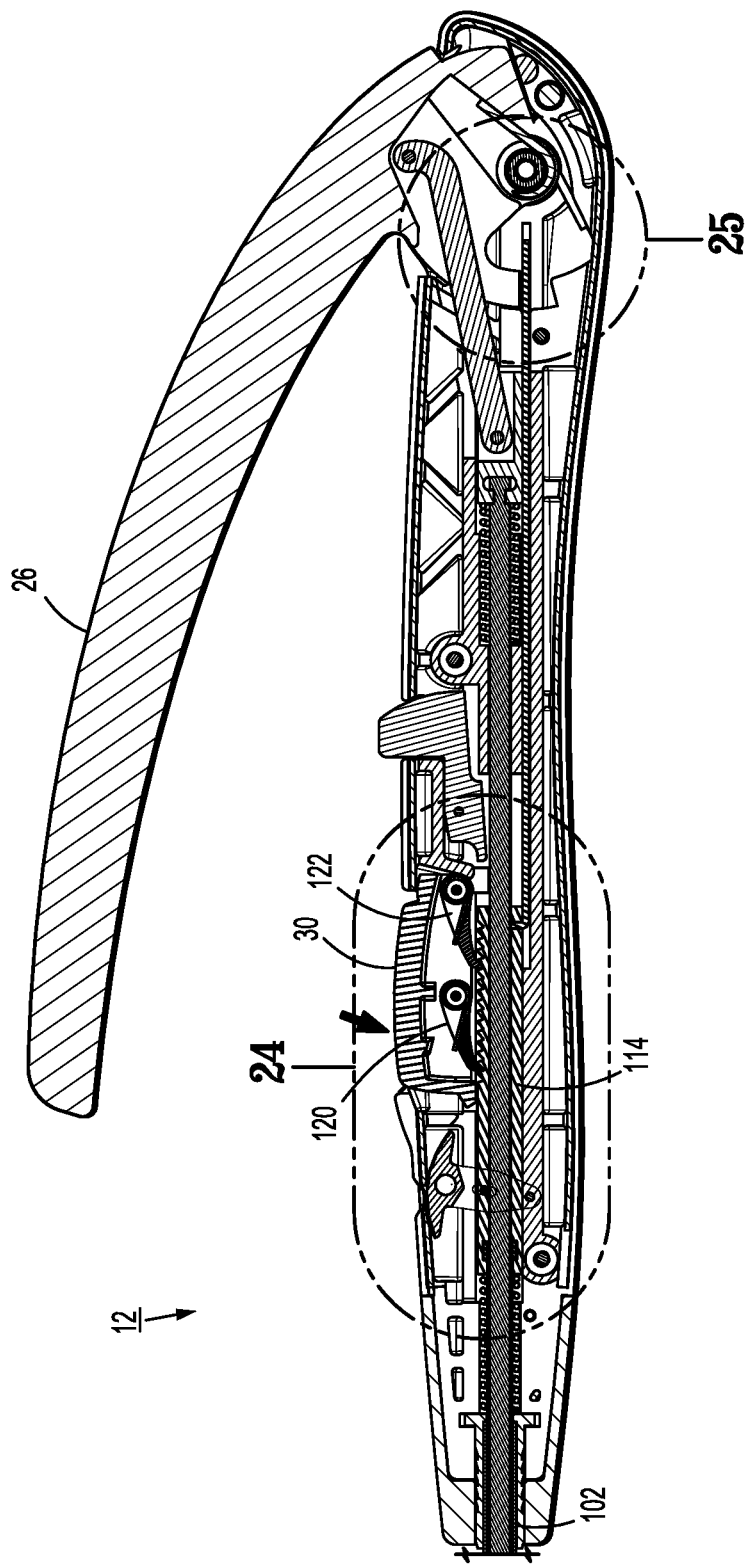
FIG. 23 is a cross sectional view of the handle assembly.

Turning now to FIGS. 23-37, and initially with regard to FIGS. 23-30, the movement of the various components of surgical device 10 will now be described. Referring to FIGS. 23 and 24, lever 26 is in the open position and advance button 30 is depressed to extend blade 20. Specifically, advance button 30 is depressed in the direction of arrow "A" against the bias of torsion springs 126 and 128 causing advance pawl 120 to drive hollow ratchet body 114 distally within handle housing 28 (FIGS. 23 and 24). Specifically, engagement tooth 260 of advance pawl 120 engages and drives a first or distal tooth 280 of ratchet teeth 124. Engagement tooth 262 of lock pawl 122 rides along ratchet teeth 124 and drops into engagement with a tooth 282 of hollow ratchet body 114 to block proximal movement of hollow ratchet body 114. Movement of hollow ratchet body 114 rotates indicator 34 such that position indicia, such as, for example, position indicia 242 is visible though window 36 in handle housing 28 (FIGS. 24 and 26). Movement of hollow ratchet body 114 additionally draws safety lock bar 172 distally within handle housing 28.

Figure 27:
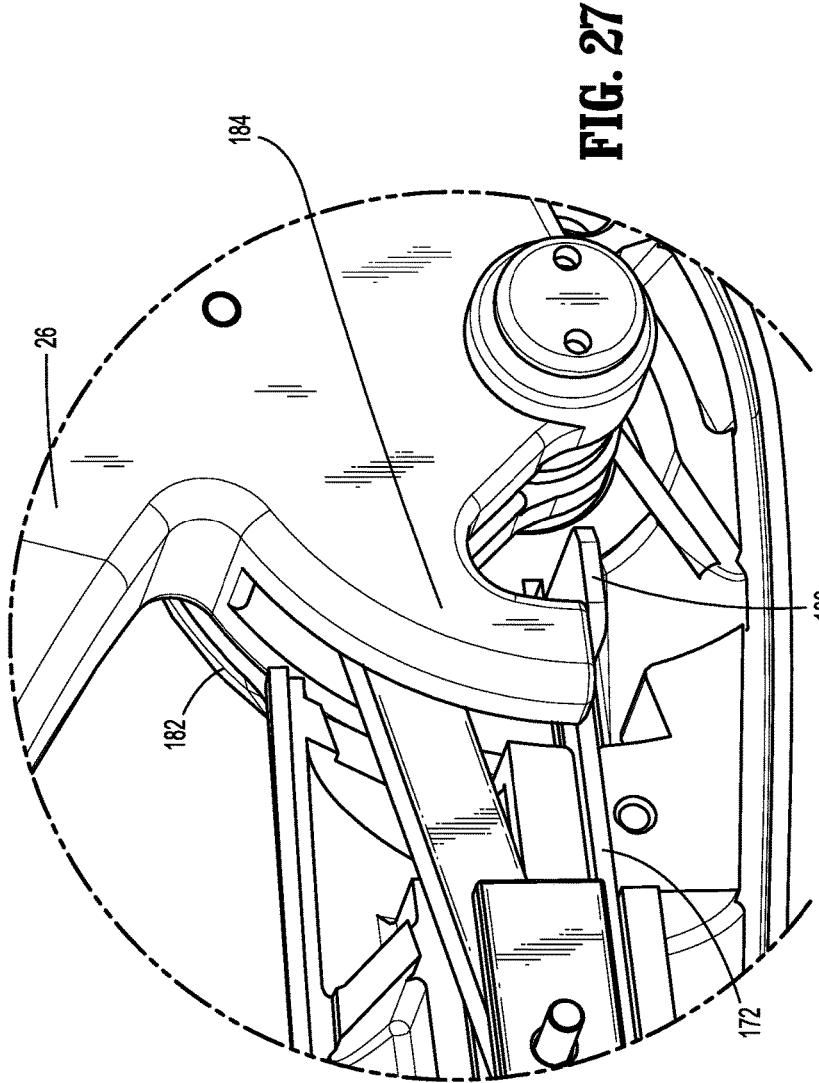
FIG. 27 is an enlarged perspective view of a portion of the handle assembly illustrating the handle lockout mechanism.
Figure 28:
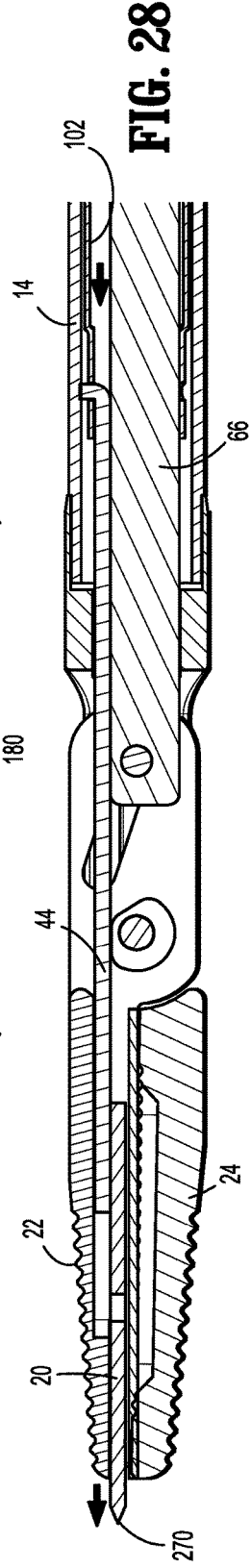
FIG. 28 is a cross sectional view of the distal end of the pediatric device illustrating blade deployment.

As shown in FIGS. 25 and 27, distally movement of safety lock bar 172 within handle housing 28 positions bar 180 beneath arms 182 and 184 of lever 26 thereby blocking or "locking out" movement of center rod 66 and preventing opening of first and second jaws 22 and 24 while blade 20 is in an extended position. Referring to FIGS. 28-30, distal movement of hollow ratchet body 114 (FIG. 24) drives intermediate tube 102 distally within elongate tubular member 14 causing elastic leaf spring 44 (FIGS. 28 and 30) to advance blade 20 a first distance out of first jaw 22 (FIGS. 28 and 29). With regard to FIGS. 29 and 30, this makes sharp radiused distal tip 270 and portions of cutting side edges 273 and 274 available for dissecting tissue. The degree of extension of blade 20 is visible from numeric indicia 276 on blade 20.

Figure 31:
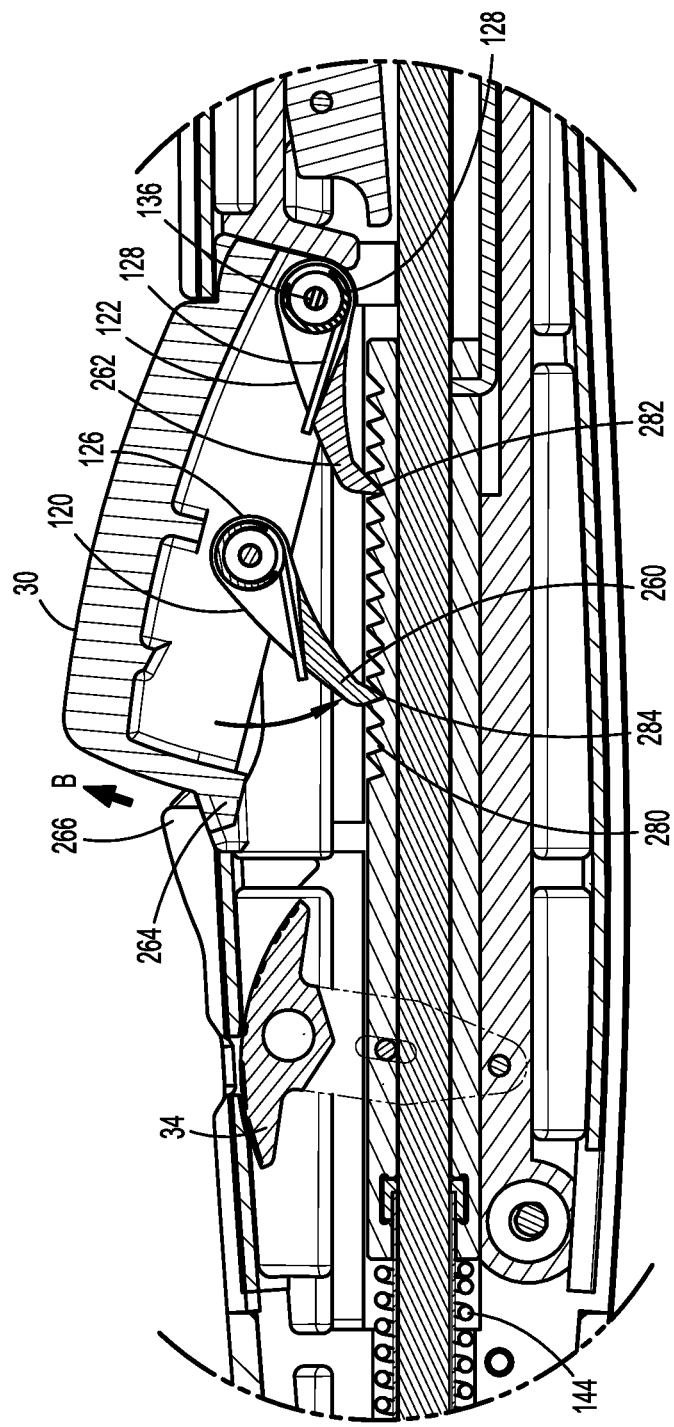
FIG. 31 is an enlarged cross sectional view of the blade deployment mechanism being reset for further advancement of the blade.

Referring to FIG. 31, as pressure is release from advance button 30, advance button is biased upward in the direction of arrow "B" by first and second torsion springs 126 and 128. This arcuate movement of advance button 30 about first pin 130 draws engagement tooth 260 of advance pawl 120 proximally along ratchet teeth 124 of hollow ratchet body 114. Lock pawl 122 remains engaged with hollow ratchet body 114 due to the bias of torsion spring 128 and common pivot about pin 136. Lock pawl 122 maintains hollow ratchet body 114 in position against the proximal bias of compression spring 144. As advance button reaches full initial height, engagement tooth 260 of advance pawl 120 drops into engagement with a second more proximal tooth 284 and is again in position to advance hollow ratchet body 114 to extend blade 20 further. Advance button 30 is blocked from lifting out of handle housing 28 by engagement of distal lip 264 with housing edge 266.

Figure 32:
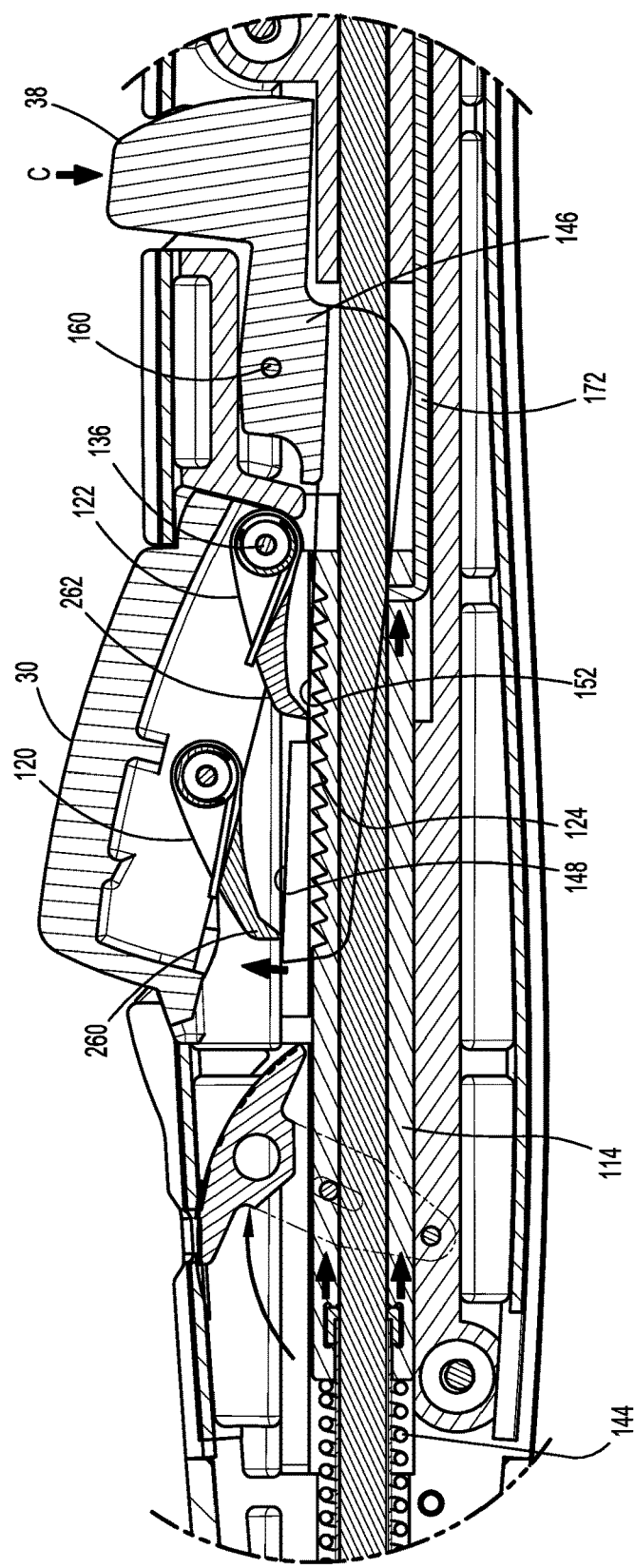
FIG. 32 is an enlarged cross sectional view similar to FIG. 31 illustrating the indicator mechanism resetting.

Referring now to FIG. 32, in order to release advance pawl 120 and, more particularly, lock pawl 122 from hollow ratchet body 114 and free up lever 26 to open and close first and second jaws 22 and 24, retract button 38 is depressed downward in the direction of arrow "C" pivoting blade retraction lever 146 about pivot pin 160. Distal lift face 148 and intermediate lift face 152 of blade retraction lever 146 are lifted up into engagement with engagement teeth 260 and 262 of advance pawl 120 and lock pawl 122 to lift them up and out of engagement with hollow ratchet body 114. Hollow ratchet body 114 is then driven proximally by the bias of compression spring 144 to draw blade 20 proximally back into first jaw 22 (FIGS. 21 and 22).

As shown, proximal movement of hollow ratchet body 114 moves safety lock bar 172 proximally within handle housing 28. This frees up lever 26 for movement.

Figure 33:
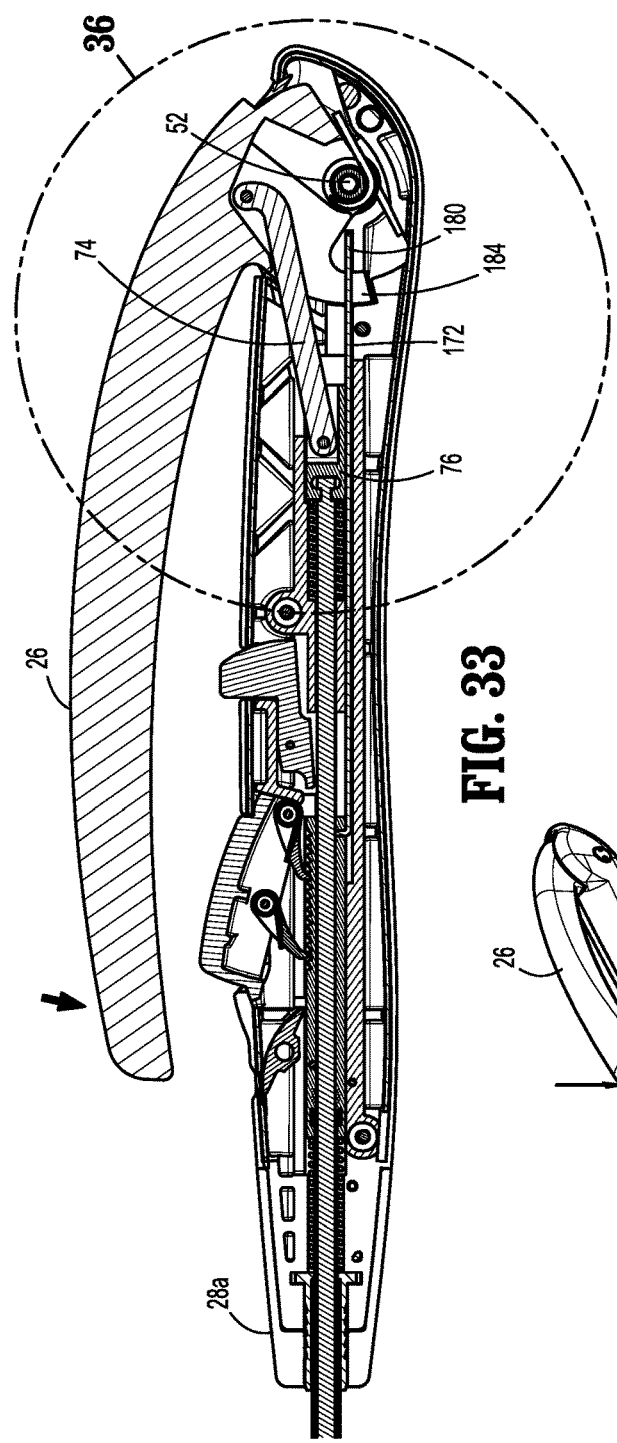
FIG. 33 is a cross sectional view of the handle assembly with the handle being actuated.
Figure 35:
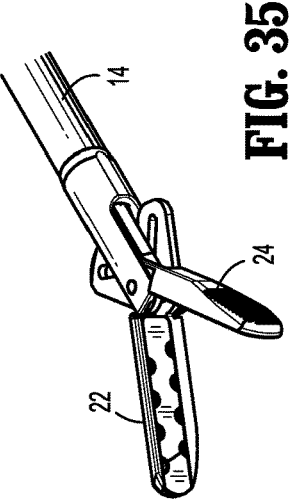
FIG. 35 is an enlarged area of detail view of FIG. 24 illustrating the jaws in the open position.
Figure 34:
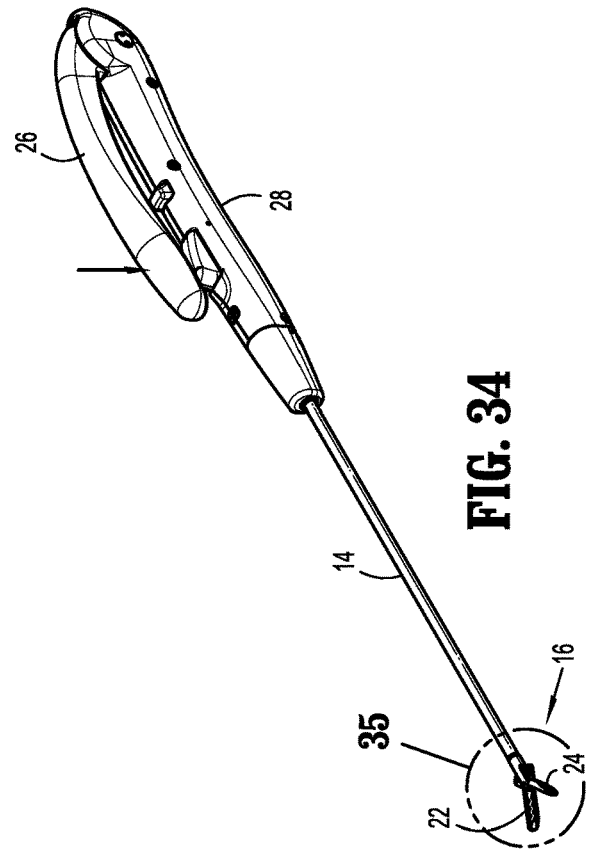
FIG. 34 is a perspective view of the pediatric device during actuation of the handle to open jaws of the end effector.

Referring to FIGS. 33-35, once lever 26 is free to move, it can be squeezed against handle housing 28 to open and close first and second jaws 22 and 24. With specific reference to FIG. 26, safety lock bar 172 is in a proximal most position within handle housing 28 with bar 180 of safety lock bar 172 positioned behind arms 182 and 84 of lever 26 thereby unlocking lever 26 for movement. Compression of lever 26 against handle housing 28 causes drive link 74 to urge slider 76 distally within handle housing 28 against the bias of compression spring 100. As distal end 94 of slider 76 moves distally, distal end 94 forces center rod 66 distally through handle housing 28 and elongate tubular member 14 (FIG. 37).

Figure 37:
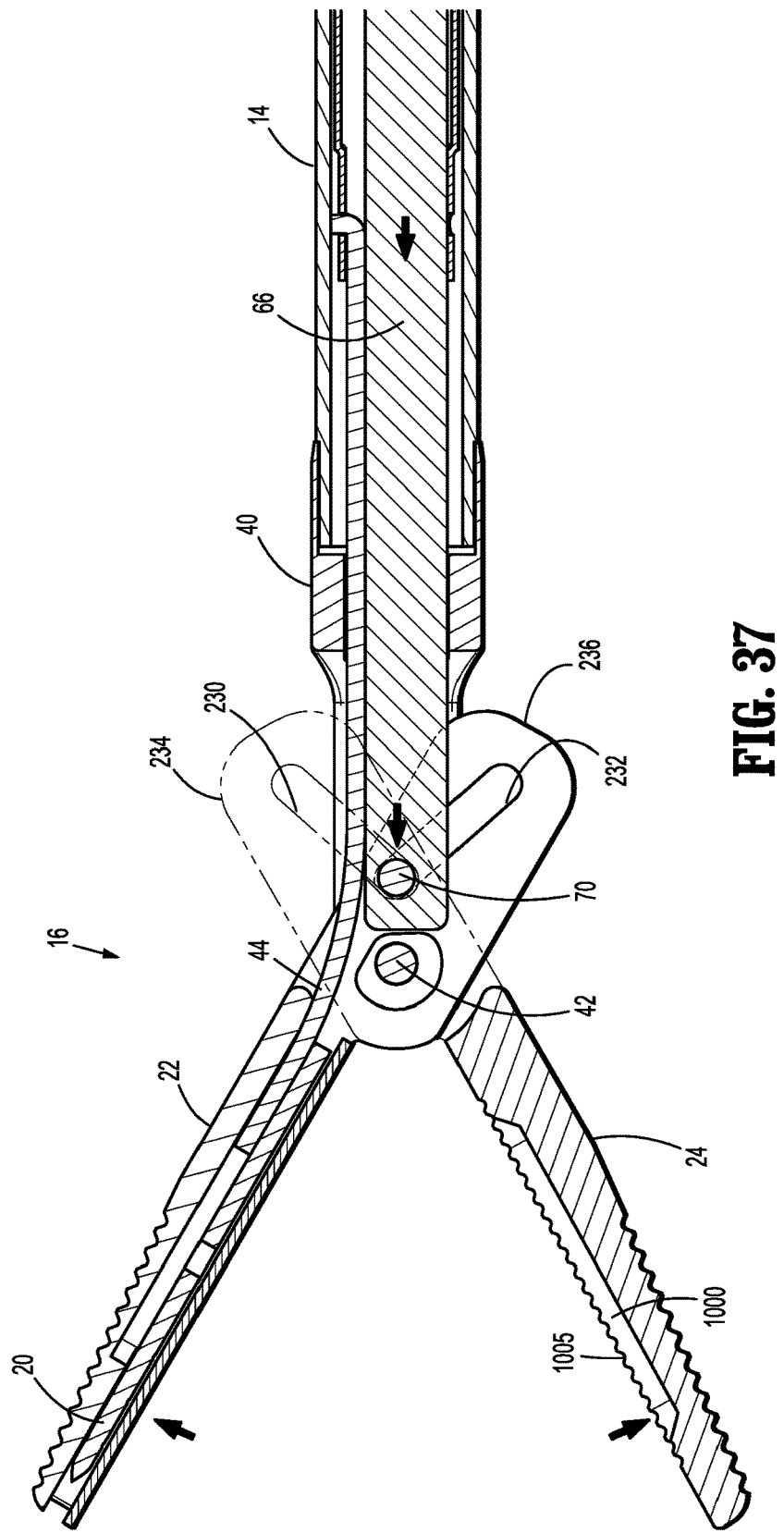
FIG. 37 is a cross sectional view of the distal end of the pediatric device with the jaws being moved to the open position.
Figure 38:
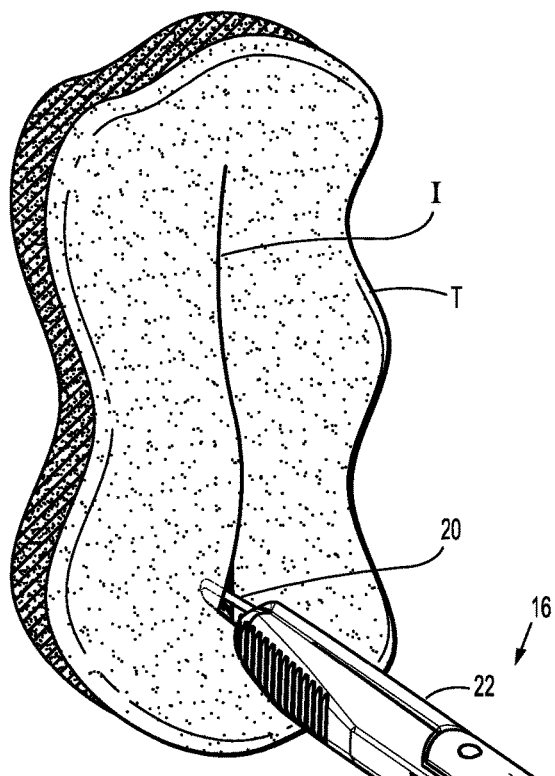
FIG. 38 is a perspective view of the distal end of the pediatric device illustrating the blade being used to make an incision in tissue.
Figure 39:
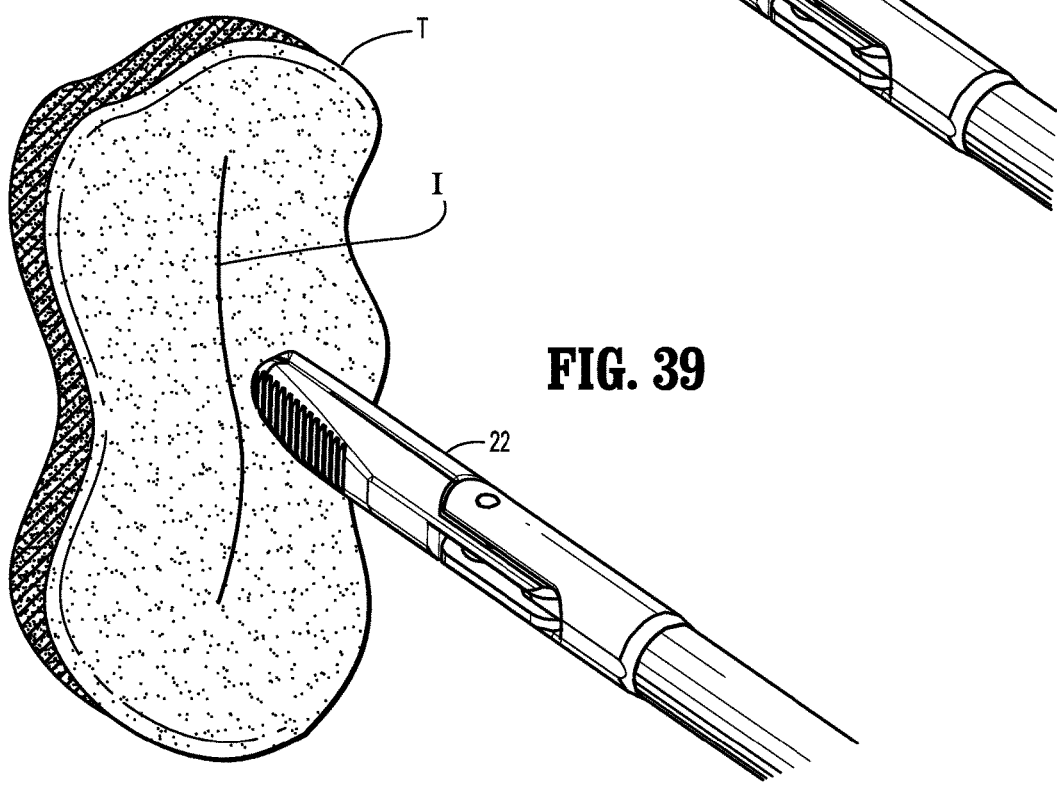
FIG. 39 is a perspective view similar to FIG. 38 with the blade retracted into the end effector.
Figure 40:
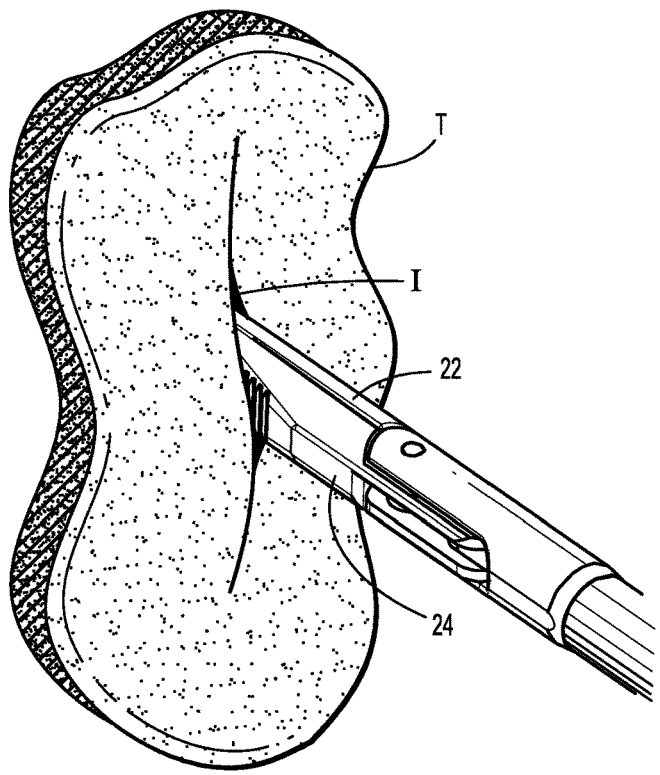
FIG. 40 is a perspective view similar to FIG. 38 with the jaws of the end effector inserted into the incision in tissue.
Figure 41:
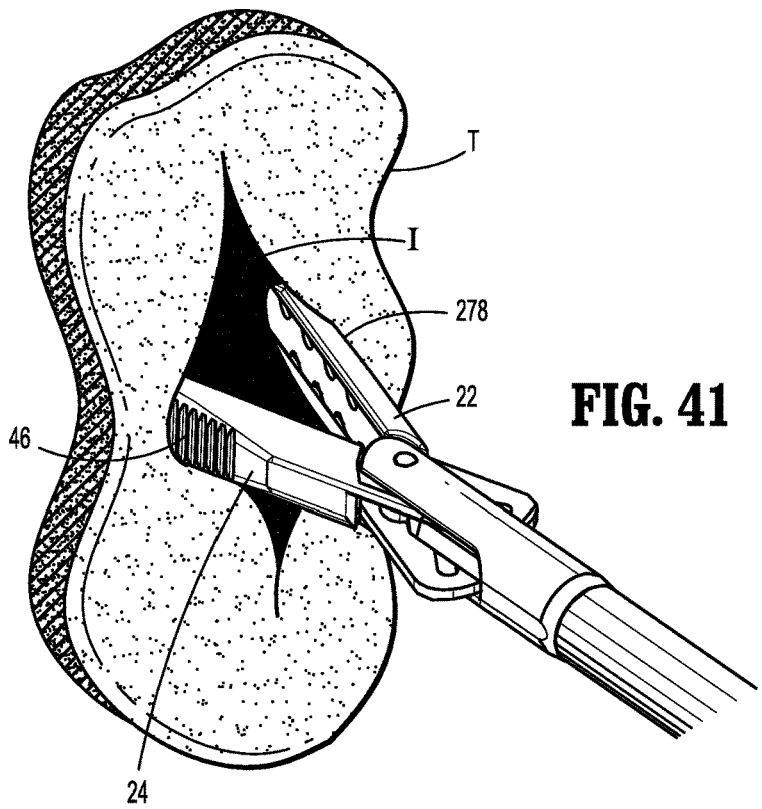
FIG. 41 is a view similar to FIG. 40 with the jaws of the end effector opened to spread the incision in the tissue.

As best shown in FIG. 37, distal movement of center rod 66 forces drive pin 79 distally moving drive pin 70 within slots 230, 232 of plates 234, 236 of second and first jaws 24 and 22 camming first and second jaws 22 and 24 from the closed position (FIG. 22) to the open position to capture and manipulate tissue. Release of pressure on lever 26 allows compression spring 100 to move center rod 66 back to the initial position camming first and second jaws 22 and 24 back to the closed position.

In this manner, surgical device 10 is able to dissect and manipulate tissue separately and safely. For example, with reference to FIGS. 1, 38-41, surgical device 10 is manipulated to position end effector 16 adjacent a tissue T. Blade 20 is extended by actuation of advance button 30 and utilized to create an incision I in tissue T. Blade 20 is then retracted by depressing retract button 38 freeing lever 26 for movement. Alternatively, blade 20 may be retracted within first jaw 22 such that first safety indicator 248 is visible through window 36. As noted above, in this position, blade 20 is safely sheathed within first jaw 22 and bar 180 of safety lock bar 172 still blocks movement of lever 26 to prevent premature opening of first and second jaws 22 and 24.

Thereafter, end effector 16 is reinserted into incision I in tissue T and lever 26 actuated to open first and second jaws 22 and 24 to spread apart incision I and create working access through tissue T. Serrations 278 and 46 on first and second jaws 22 and 24, respectively, aid in gripping and spreading apart incision I. The second jaw 24 has serration 1005 on the inside too, so the device can also grasp the tissue. Additionally, jaw 24 has a subflush area 1000 to improve grasping. See FIG. 37. The plate 210 also has a wavy shape 214, 212 to create an uneven feature for better grasping. See FIG. 9.

Figure 42:
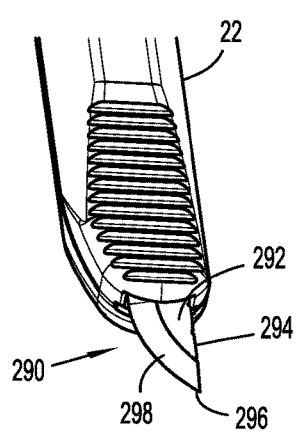
FIG. 42 is a perspective view of a distal end of the end effector illustrating one embodiment of a blade having a single edge geometry.
Figure 43:
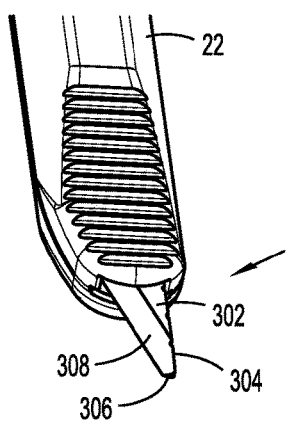
FIG. 43 is a view similar to FIG. 42 illustrating an alternative, single edge blade geometry.
Figure 44:
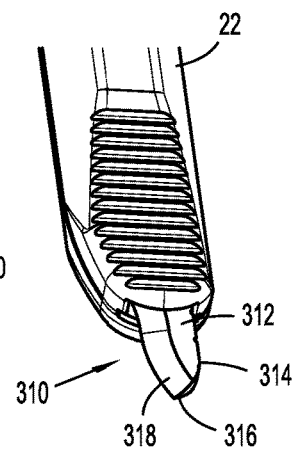
FIG. 44 is a view similar to FIG. 42 illustrating a further single edge blade geometry.
Figure 45:
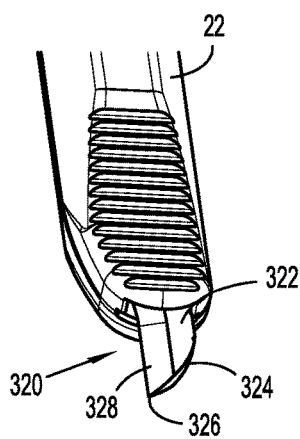
FIG. 45 is a view similar to FIG. 42 illustrating yet a further alternative single edge blade geometry.
Figure 46:
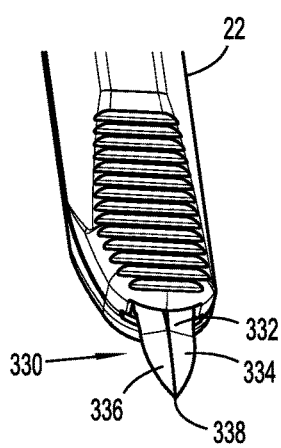
FIG. 46 is a view similar to FIG. 42 illustrating a blade having a double edge blade geometry.
Figure 47:
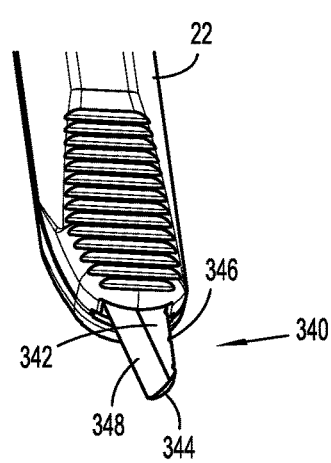
FIG. 47 is a view similar to FIG. 42 illustrating a blade having a wedge shaped geometry.

Referring to FIGS. 42-47, there are disclosed various embodiments of blade configurations for use with end effector 16. FIG. 42 illustrates a blade 290 including a body 292 having a flat back 294, a sharp distal cutting tip 296 and a single, arcuate or concave cutting edge 298. FIG. 43 illustrates a blade 300 including a body 302 having a flat back 304, a small, blunt tip 306 and a relatively straight cutting edge 308. FIG. 44 illustrates a blade 310 including a body 312 having a curved, blunt back 314, a sharp distal tip 316 and a wavy or sinusoidal cutting edge 318. FIG. 45 illustrates a blade 320 including a curved back 322, a sharp tip 326 and a straight or flat cutting edge 328. FIG. 46 illustrates a stiletto type blade 330 including a body 332 having first and second symmetrical cutting edges 334 and 336, respectively, and a sharp distal tip 338. FIG. 47 illustrates a blade 340 including a body 342 having a sharp, vertical dissecting tip 344, a curved back 346 and an angled cutting edge 348.

Figure 48:
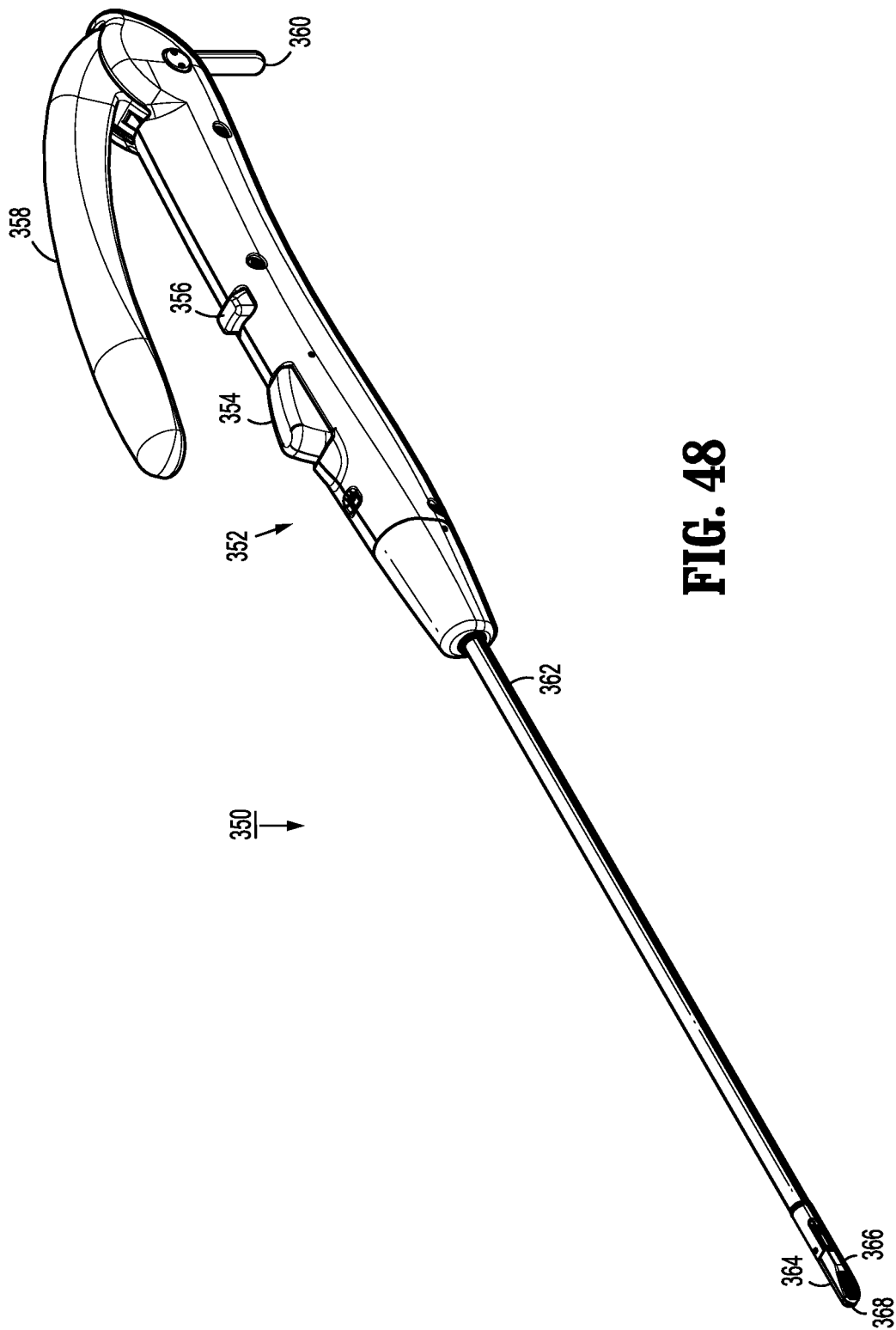
FIG. 48 is a perspective view of an alternative embodiment of the disclosed pediatric device incorporating cautery capabilities.

Referring now to FIG. 48, there is disclosed an alternative embodiment of a surgical device 350 incorporating cauterizing capabilities. Surgical device 350 is substantially similar to surgical device 10 described hereinabove and generally includes a handle assembly 352 having an advance button 354, a retract button 356 and a lever 358. Handle assembly 352 additionally includes a cautery fitting or connector 360 for connection to a source of heat or electrical power. An insulated elongate tubular member 362 extends from handle assembly 352 and ends in movable first and second jaws 364 and 366. A blade 368 is movably mounted in first jaw 364 in a manner similar to first jaw 22 described herein above. Blade 368 is connected to connector 360 and electrically isolated from first jaw 364. Blade 368 may include a cutting edge (not shown) or be formed blunt.

Figure 49:
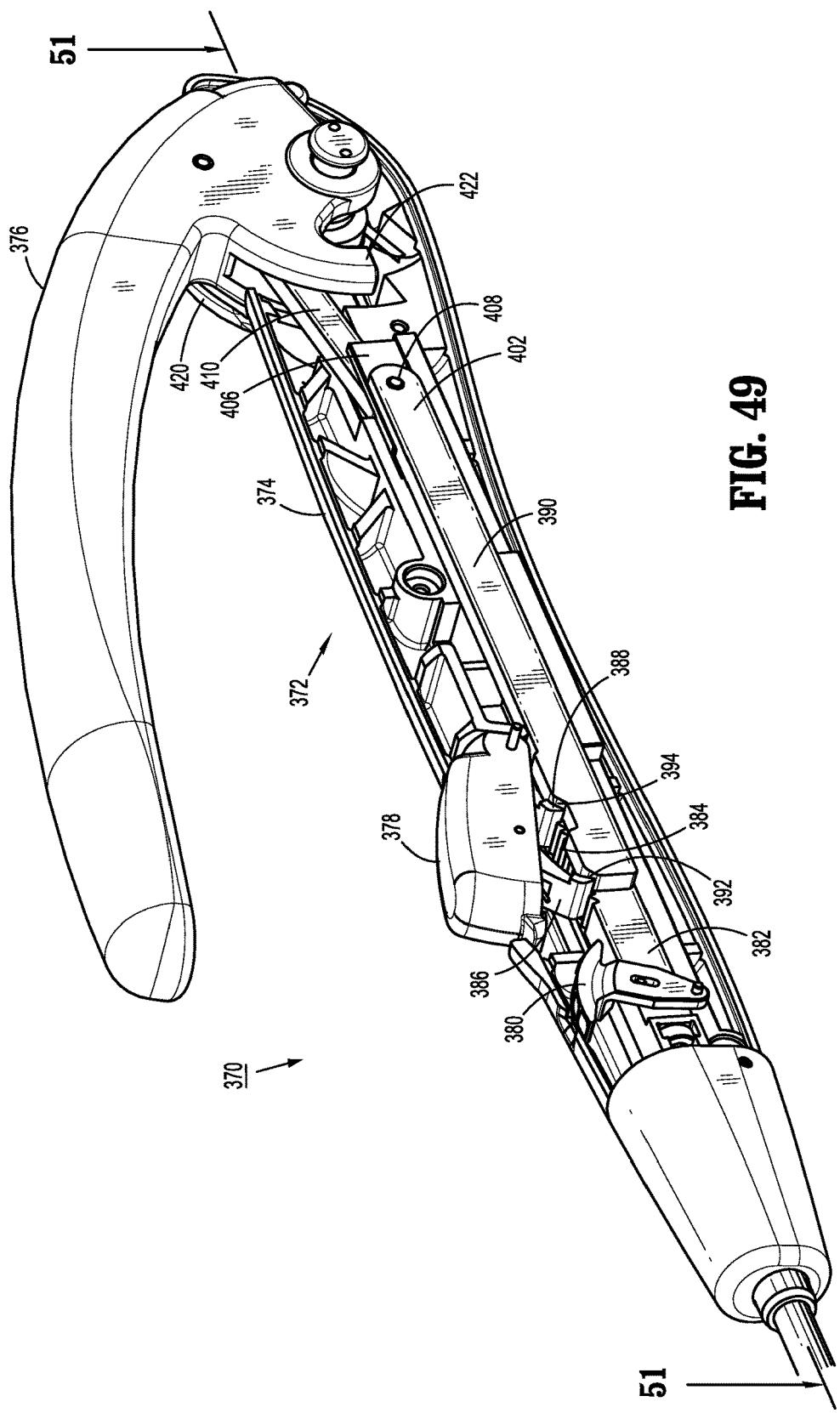
FIG. 49 is a perspective view of an alternate embodiment of a handle assembly for use in the pediatric device.
Figure 50:
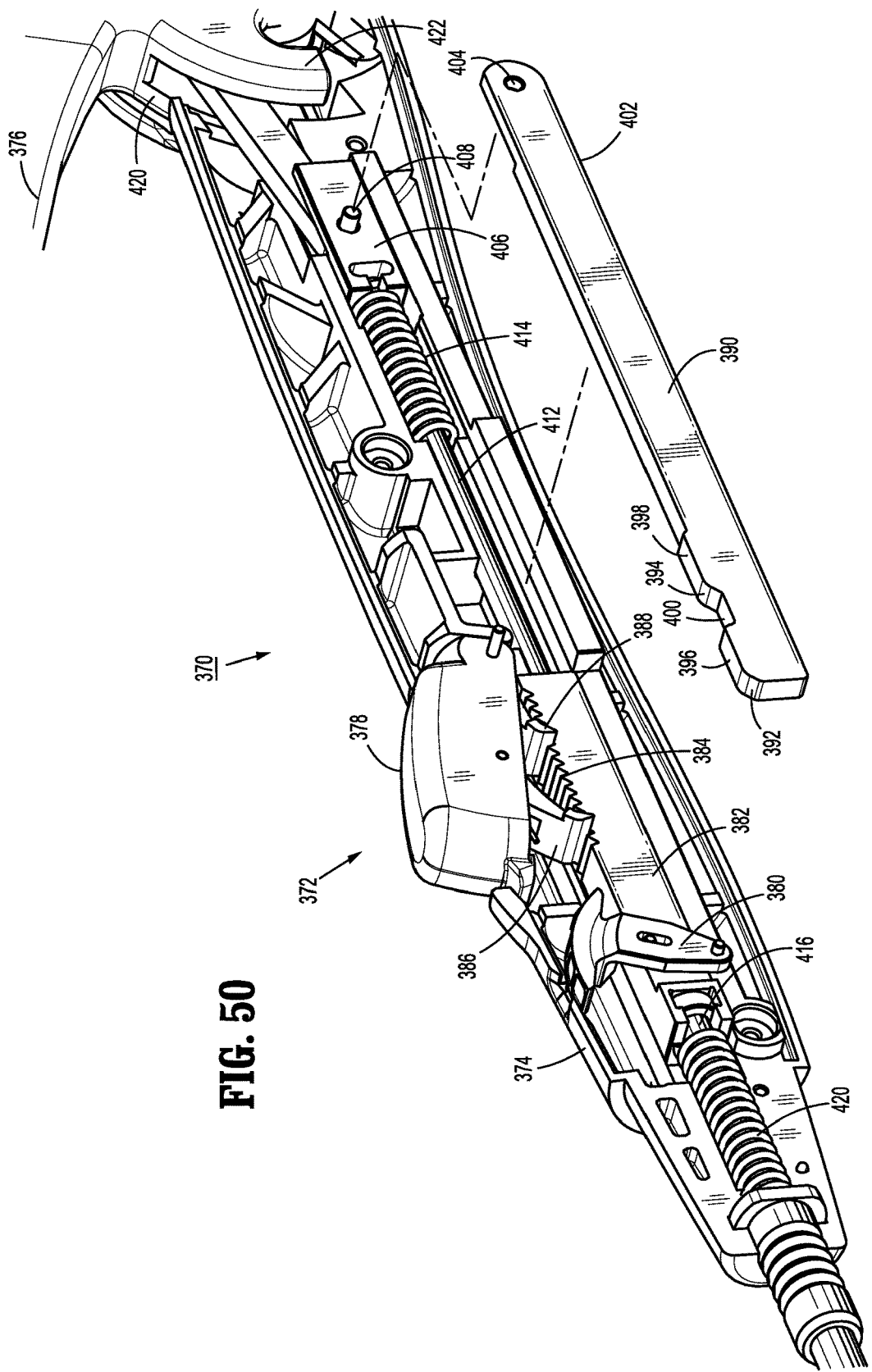
FIG. 50 is a perspective view, with a part separated, similar to FIG. 49.
Figure 51:
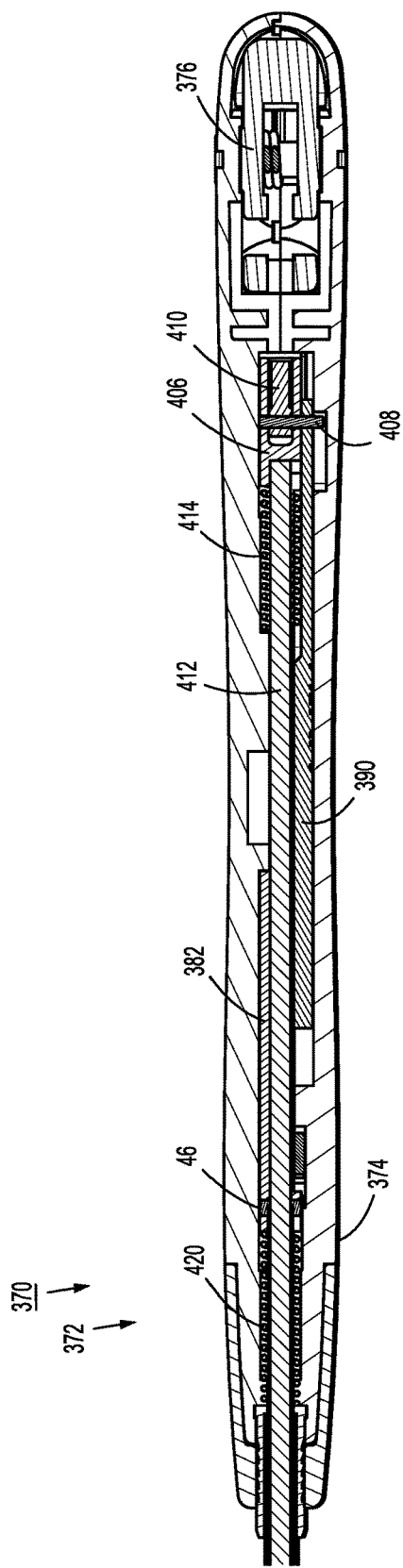
FIG. 51 is a top plan cross sectional view of the handle assembly of FIG. 49.

Referring now to FIGS. 49-51, there is disclosed an alternative embodiment of a surgical device 370 for use in pediatric surgery. Surgical device 370 is substantially structurally and functionally similar to surgical device 10 described hereinabove and generally includes a handle assembly 372 having a handle housing 374, a jaw operating lever 376 and an advance button 378 for extending a blade out of a first jaw (not shown) in a manner identical to that described hereinabove. An indicator 380 is visible through handle housing 374 and is connected to a hollow ratchet body 382 having ratchet teeth 384. An advance pawl 386 is connected to advance button 378 to engage and drive hollow ratchet body 382 distally within handle housing 374. A lock pawl 388 is also provided to maintain hollow ratchet body 382 in the distal position until released.

In contrast to surgical device 10, surgical device 370 incorporates a cam release bar 390 in place of blade retraction lever 146 described hereinabove. Cam release bar 390 includes first and second cam surfaces or edges 392 and 394 for lifting advance pawl 386 and lock pawl 388, respectively, out of engagement with ratchet teeth 384 on hollow ratchet body 382. Relatively flat support surfaces 386 and 388 are located immediately proximal to cam edges 392, 394 to maintain advance and lock pawls 396 and 388 out of engagement with hollow ratchet body 382 during operation of lever 376 to open and close a pair of jaws. A short depression 400 is located between support surfaces 396, 398 to allow lock pawl 388 to engage hollow ratchet body 382 when cam release bar 390 is in a proximal position.

In order to drive cam release bar 390 against advance and lock pawls 386, 388, a proximal end 402 of cam release bar 390 includes a hole 404 and is connected to a slider 406 by a pin 408. Similar to slider 76 above, slider 406 is connected through a link 410 to lever 376. As best shown in FIGS. 50 and 51, slider 406 is connected to a center rod 412 and biased proximally by a compression spring 414. Hollow ratchet body 382 is connected to an intermediate tube 416 and biased proximally by a compression spring 420.

In operation, advance button 378 is operated to advance a blade out of a first jaw (not shown) in a manner identical to that described hereinabove. When a surgeon needs to retract the blade, slight pressure on lever 376 advances cam release bar 390 distally causing cam edges 392, 394 to lift advance and lock pawls 386, 388 out of engagement with ratchet teeth 384 on hollow ratchet body 382. The engagement of cam edges 392 and 394 with advance pawl 386 and lock pawl 388, respectively, is timed to allow the blade to retract due to the bias of compression spring 420 prior to the jaws moving in response to distal movement of center rod 412. Support surfaces 396, 398 maintain advance and lock pawls 386, 388 out of engagement during operation of lever 376 to open an close a pair of jaws. When lever 376 is released to allow the jaws to close, cam release bar 390 is drawn to the proximal most position allowing advance and lock pawls 386,388 to again engage hollow ratchet body 382. It should be noted that a safety lock bar (not shown) similar to safety lock bar 172 described above may be incorporated into surgical device 370 by modifying arms 420 and 422 of lever 376 to be slightly shorter and allowing the initial movement of lever 376 to drive cam release bar 390 through its initial motion releasing hollow ratchet body 382.

In this manner, surgical device 390 eliminates a button simplifying use while maintaining safety features.

It will be understood that various modifications may be made to the embodiments disclosed herein. For example, one of the first or second jaws may be formed stationary with the elongate tubular member. Further, a rotatable wheel, pivotal switch, etc. may be substituted for the disclosed advance button. Additionally, both the first and second jaws may include blades and the advancement mechanism duplicated or connected to both blades. Internal seals may be provided to ensure sealing of the device in the cavity and a stopcock is envisioned to help flush the device if it is provided as a reusable device. Therefore, the above description should not be construed as limiting, but merely as exemplifications of particular embodiments. Those skilled in the art will envision other modifications within the scope and spirit of the claims appended hereto.

The invention claimed is:

1. A combination surgical device comprising:
   an elongate tubular member having a distal portion;
   an end effector assembly coupled to the distal portion of the elongate tubular member, the end effector assembly including:
   a first jaw having a first tissue contacting surface;
   a second jaw having a second tissue contacting surface opposing the first tissue contacting surface, the first and second tissue contacting surfaces configured to grasp tissue therebetween; and
   a blade movably mounted within the first jaw, the blade being flat and disposed in an orientation parallel to the first tissue contacting surface, the blade being configured to dissect tissue beyond a distal end of the first jaw; and
   an advancement mechanism for extending the blade out of the first jaw, the advancement mechanism including a hollow body and an advance pawl mounted within the hollow body.

2. The surgical device according to claim 1, wherein the hollow body includes ratchet teeth engageable by the advance pawl to incrementally advance the blade relative to the first jaw.

3. The surgical device according to claim 1, wherein the advancement mechanism is connected to the blade by an intermediate tube movably mounted within the elongate tubular member.

4. The surgical device according to claim 3, wherein the hollow body is connected to a proximal region of the intermediate tube and an advance button movably mounted in a handle and engageable with the hollow body to drive the hollow body distally within the handle.

5. The surgical device according to claim 4, wherein the advance pawl is rotatably mounted to the advance button and the ratchet teeth are engageable by the advance pawl to incrementally advance the hollow body distally within the handle in response to actuation of the advance button such that the blade is incrementally advanced through the first jaw.

6. The surgical device according to claim 5, wherein the advance button is pivotally mounted on the handle at a pivot point and the advancement mechanism further includes a lock pawl engageable with the ratchet teeth and sharing the pivot point with the advance button such that the lock pawl remains engaged with the ratchet teeth upon release of the advance button.

7. The surgical device according to claim 6, further comprising a blade retraction lever movably mounted on the handle and having a first lift face engageable with the advance pawl and a second lift face engageable with the lock pawl such that actuation of the blade retraction lever lifts the advance pawl and lock pawl out of engagement with the ratchet teeth.

8. The surgical device according to claim 7, further comprising a cam release bar movably mounted within the handle and connected to the blade retraction lever, the cam release bar having a first cam edge engageable with the advance pawl and a second cam edge engageable with the lock pawl such that actuation of the blade retraction lever drives the cam release bar distally within the handle to lift the advance pawl and lock pawl out of engagement with the ratchet teeth.

9. The surgical device according to claim 1, wherein the first jaw has a body including a back, a first side, and a second side which define a channel for receipt of the blade.

10. The surgical device according to claim 9, wherein the first jaw further includes a retention plate covering the channel.

11. A combination surgical device comprising:
    an elongate tubular member;
    an end effector assembly supported by the elongate tubular member, the end effector assembly including a first jaw and a second jaw movably mounted relative to the first jaw, the first and second jaws defining opposing tissue contacting surfaces, the first jaw further including a blade movably mounted therewithin, the blade being flat and disposed parallel to the tissue contacting surface of the first jaw; and
    an advancement mechanism positioned within a handle, the advancement mechanism including a ratchet body operable to extend the blade out of the first jaw.

12. The surgical device according to claim 11, wherein the blade is extendable beyond a distal end of the first jaw.

13. The surgical device according to claim 11, further comprising a lever movably mounted on a handle and connected to the first and second jaws, the lever operable to move the first and second jaws from a closed position in which the first and second jaws are in close cooperative alignment to an open position in which the first and second jaws are spaced apart to receive tissue.

14. The surgical device according to claim 13, wherein the lever is connected to the first and second jaws by a center rod.

15. The surgical device according to claim 14, wherein the center rod is biased proximally by a compression spring, the compression spring additionally biasing the lever to an open position.

16. The surgical device according to claim 11, further comprising an indicator disposed on a handle and connected to the advancement mechanism, the indicator having markings corresponding to a degree of extension of the blade out of the first jaw.

17. The surgical device according to claim 16, wherein the blade has indicia corresponding to the degree of extension out of the first jaw.

18. The surgical device according to claim 11, further comprising an electrical connector on a handle for supplying cauterizing current to the blade.

19. A combination surgical device comprising:
    an elongate tubular member;
    an end effector assembly supported by the elongate tubular member, the end effector assembly including a first jaw and a second jaw movably mounted relative to the first jaw, the first and second jaws defining opposing tissue contacting surfaces, the first jaw further including a blade movably mounted therein, the blade being flat and disposed parallel to the tissue contacting surface of the first jaw; and
    an advancement mechanism for extending the blade out of the first jaw, the advancement mechanism including a hollow body and an advance pawl mounted within the hollow body.

* * * * *